US 10,258,701 B2

United States Patent
Chen et al.

(10) Patent No.: US 10,258,701 B2
(45) Date of Patent: Apr. 16, 2019

(54) LABELED EVANS BLUE DYE DERIVATIVE FOR IN VIVO SERUM ALBUMIN LABELING

(71) Applicant: The United States of America, as represented by the Secretary, Department of Health and Human Services, Washington, DC (US)

(72) Inventors: Xiaoyuan Chen, Potomac, MD (US); Lixin Lang, North Potomac, MD (US); Gang Niu, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/587,948

(22) Filed: May 5, 2017

(65) Prior Publication Data
US 2017/0239376 A1 Aug. 24, 2017

Related U.S. Application Data

(62) Division of application No. 14/675,364, filed on Mar. 31, 2015, now abandoned.

(51) Int. Cl.
| A61K 51/04 | (2006.01) |
| C09B 45/00 | (2006.01) |
| C07B 59/00 | (2006.01) |
| C09B 29/30 | (2006.01) |

(52) U.S. Cl.
CPC ........ *A61K 51/0482* (2013.01); *C07B 59/004* (2013.01); *C09B 29/30* (2013.01); *C09B 45/00* (2013.01)

(58) Field of Classification Search
CPC .......... A61K 51/00; C09B 45/00; C09B 29/00
See application file for complete search history.

(56) References Cited

U.S. PATENT DOCUMENTS

| 2010/0081939 A1 | 4/2010 | Chu |
| 2011/0085969 A1 | 4/2011 | Rollo et al. |
| 2013/0309169 A1* | 11/2013 | Kim ..................... A61K 51/081 424/1.69 |

OTHER PUBLICATIONS

Tatsuhiro Yamamoto et al., First Functional MRI Contrast Agent Recognizing Vascular Lesions, Analytical Sciences, vol. 20, 5-7. (Year: 2004).*
Jae Yeon Choi et al., Development of 68Ga-labeled mannosylated human serum albumin (MSA) as a lymph node imaging agent for positron emission tomography, Nuclear Med and Biol, 38, 371-379. (Year: 2011).*
Anderson et al., "Evaluation of copper-labeled Bifunctional Chelate-Albumin conjugates for blood pool imaging," *Nucl. Med. Biol.*, 20(4), 461-467 (1993).
Chen et al., MicroPET imaging of brain tumor angiogenesis with $^{18}$F-labeled PEGylated RGD peptide, *Eur. J. Nucl. Med. Mol. Imaging*, 31 (8), 1081-1089 (2004).
Elsadek et al., "Impact of albumin on drug delivery—new applications on the horizon," *J. Control Release*, 157 (1), 4-28 (2012).
Hirano et al., "A comparison of indocyanine green fluorescence imaging plus blue dye and blue dye alone for sentinel node navigation surgery in breast cancer patients," *Ann. Surg. Oncol.*, 19 (13), 4112-4116 (2012).
Hoffend et al., "Gallium-68-DOTA-albumin as a PET blood-pool marker: experimental evaluation in vivo," *Nucl. Med. Biol.*, 32 (3), 287-292 (2005).
Klohs et al., "Near-infared fluorescence imaging with fluorescently labeled albumin: a novel method for non-invasive optical imaging of blood-brain barrier impairment after focal cerebral ischemia in mice," *J. Neurosci. Methods*, 180 (1), 126-132 (2009).
Koo et al., "In vivo non-ionizing photoacoustic mapping of sentinel lymph nodes and bladders with ICG-enhanced carbon nanotubes," *Phys. Med. Biol.*, 57 (23), 7853-7862 (2012).
Lauffer et al., "MS-325: albumin-targeted contrast agent for MR angiography," *Radiology*, 207 (2), 529-538 (1998).
McAfee et al., "$^{99M}$Tc labeled serum albumin for scintillation scanning of the placenta" *J. Nucl. Med.*, 5, 936-946 (1964).
Niu et al., "In Vivo Labeling of Serum Albumin for PET," *J. Nucl. Med.*, 55 (7), 1150-1156 (2014).
Okazawa et al., "Measurement of regional cerebral plasma pool and hematocrit with copper-62-labeled HSA-DTS," *J. Nucl. Med.*, 37 (7), 1080-1085 (1996).
Porenta et al., "Parameter estimation of cardiac geometry by ECG-gated PET imaging: validation using magnetic resonance imaging and echocardiography," *J. Nucl. Med.*, 36 (6), 1123-1129 (1995).
Strand et al., Influence of Macrocyclic Chelators on the Targeting Properties of 68Ga-labeled Synthetic Affibody Molecules: Comparison with 111In-Labeled Counterparts, PLOS ONE, 8(8): 1-10 (2013).
Veronesi et al., "Sentinel-node biopsy to avoid axillary dissection in breast cancer with clinically negative lymph-nodes," *Lancet.*, 349 (9069), 1864-1867 (1997).
Wang et al., "In vivo albumin labeling and lymphatic imaging," *Proc. Natl. Acad. Sci. U.S.A.*, 112 (1), 208-213 (2015).
Wängler et al., "Kit-like $^{18}$F-labeling of proteins: synthesis of 4-(Di-tert-butyl[$^{18}$F]fluorosilyl)benzenethiol (Si[$^{18}$F]FA-SH) labeled rat serum albumin for blood pool imaging with PET," *Bioconjug. Chem.*, 20 (2), 317-321 (2009).
Yamamoto et al., "First functionalized MRI contrast agent recognizing vascular lesions," *Anal. Sci.*, 20 (1), 5-7 (2004).

* cited by examiner

*Primary Examiner* — Michael G. Hartley
*Assistant Examiner* — Jagadishwar R Samala
(74) *Attorney, Agent, or Firm* — Leydig, Voit & Mayer, Ltd.

(57) ABSTRACT

Disclosed is a compound of formula (I):

$$B-A-\overset{H}{N}-L-N=N-\underset{R^5\ R^4}{\overset{R^1\ R^2}{\text{[naphthalene]}}}-R^3 \cdot M_n$$

(I)

wherein L, $R^1$-$R^5$, A, B, M, and n are as defined in the specification, as well as a method of preparing the compound. Also disclosed are a method of blood-pool imaging in a mammal and a method of imaging a lymph node in a mammal, comprising use of the compound.

5 Claims, 25 Drawing Sheets

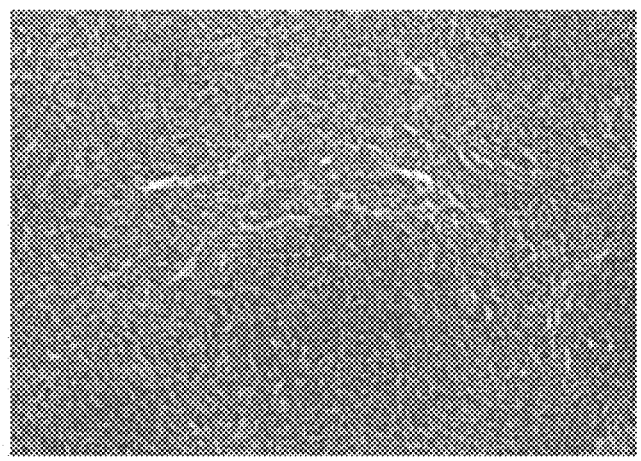
FIG. 18C
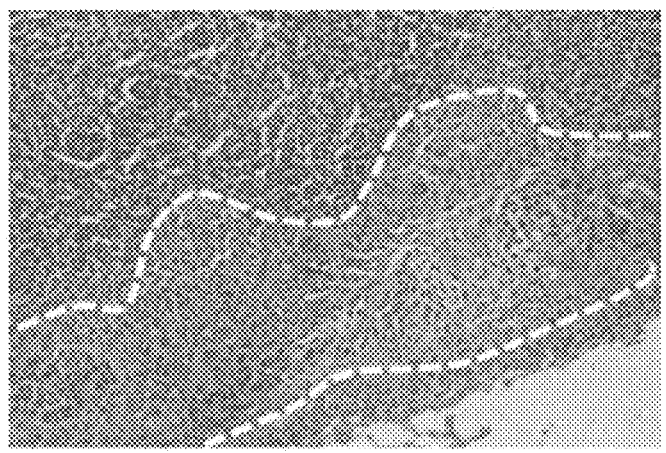
FIG. 18D
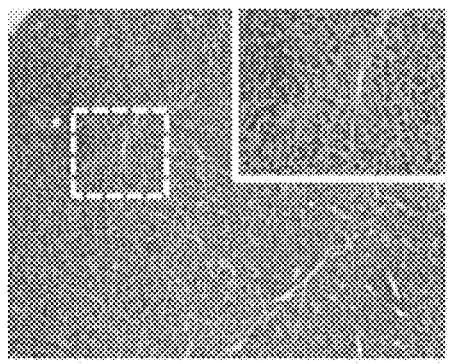 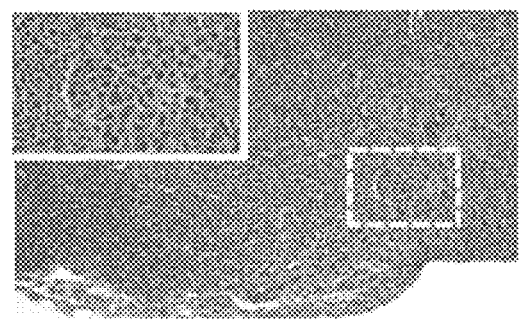
FIG. 18E                    FIG. 18F 90 min Bright field

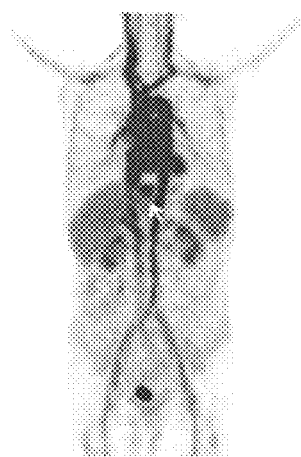
FIG. 29A
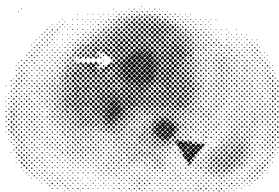  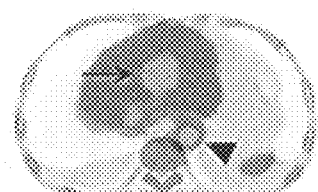
FIG. 29B  FIG. 29C  FIG. 29D
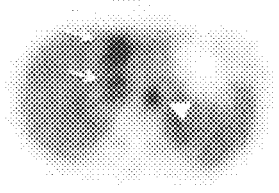 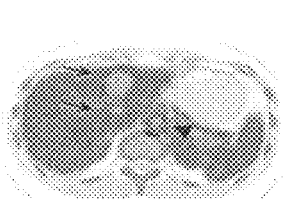 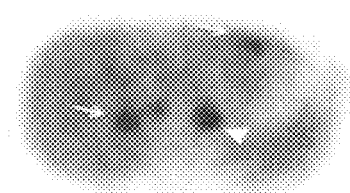
FIG. 29E  FIG. 29F  FIG. 29G
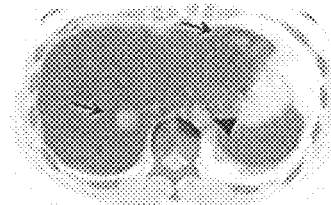
FIG. 29H

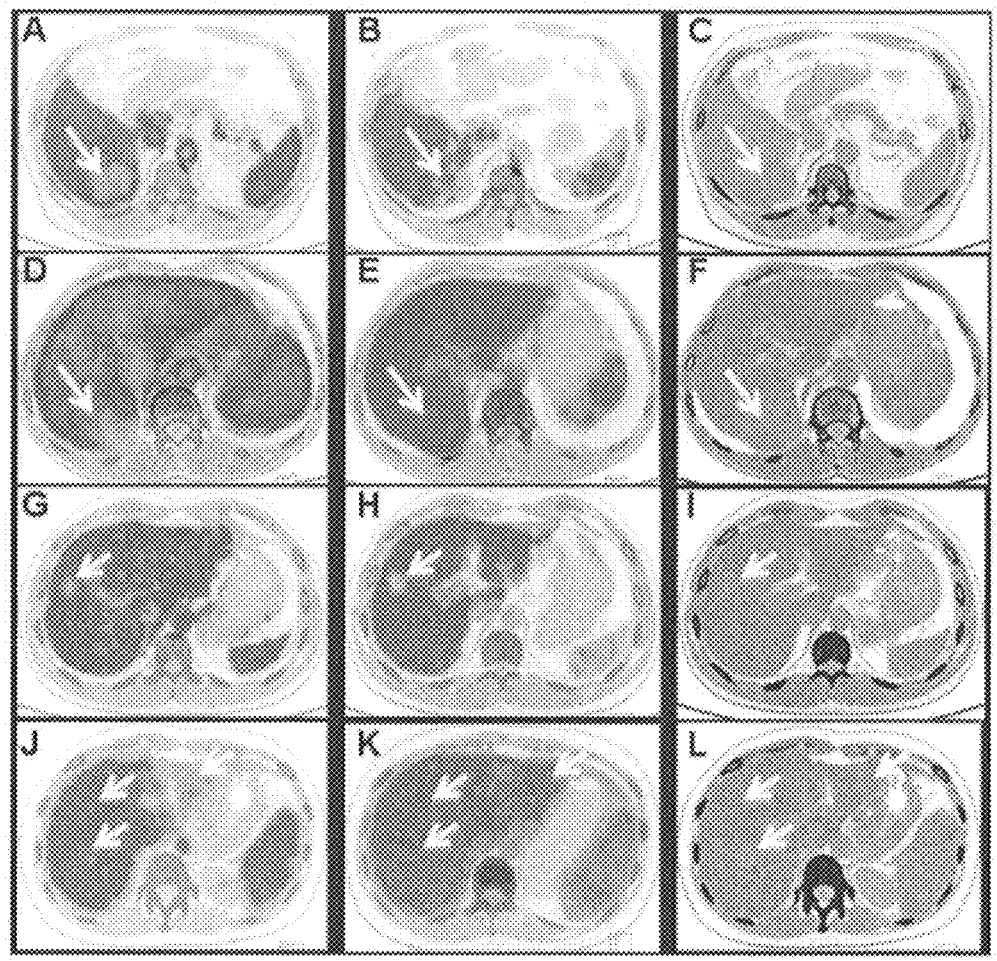
FIG. 30
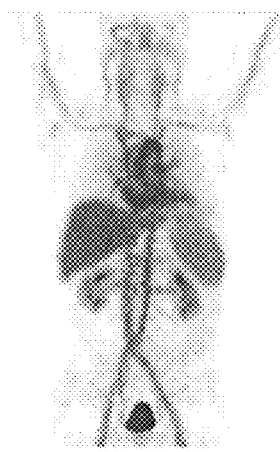
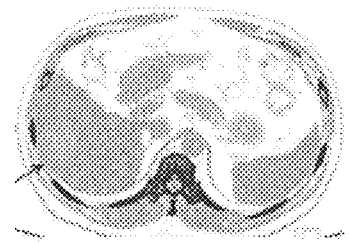
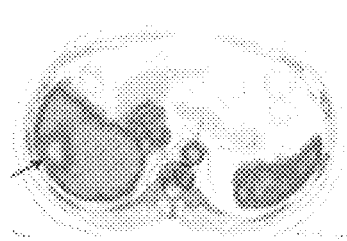
FIG. 31A      FIG. 31B      FIG. 31C

LABELED EVANS BLUE DYE DERIVATIVE FOR IN VIVO SERUM ALBUMIN LABELING

CROSS REFERENCE TO A RELATED APPLICATION

This patent application is a divisional of copending U.S. patent application Ser. No. 14/675,364, filed Mar. 31, 2015, the disclosure of which is incorporated by reference for all intents and purposes.

BACKGROUND OF THE INVENTION

As the most abundant plasma protein, serum albumin has emerged as a versatile carrier for therapeutic agents, primarily for treating diabetes, cancer, rheumatoid arthritis and infectious diseases (Elsadek B et al., Kratz F. *J Control Release* 2012; 157(1): 4-28). Serum albumin was also used directly as an imaging probe after labeling with fluorescent dyes for optical imaging (Klohs J. et al., *J Neurosci Methods*. 2009; 180(1): 126-132), radioisotopes for scintillation scanning or positron emission tomography (PET) (McAfee J G et al., *J Nucl Med* 1964; 5:936-946; Hoffend J. et al., *Nucl Med Biol* 2005; 32(3): 287-292), or $Gd^{3+}$ for magnetic resonance imaging (MRI) (Lauffer R B et al., *Radiology*. 1998; 207(2): 529-538). The major applications of labeled serum albumin mentioned above include blood pool imaging and angiography.

In clinical nuclear medicine, kit preparations for indirect and direct $^{99m}$Tc-radiolabeling of red blood cells (RBCs) are still the dominant methods for blood pool imaging. Compared with single-photon emission computed tomography (SPECT), PET is more sensitive and has higher spatial resolution with clinical instruments. However, to date, only very few blood-pool tracers have been introduced for PET. For example, carbon monoxide (CO) containing either $^{11}$C or $^{15}$O has been used to label RBCs for PET. However, due to their short half-lives (20.4 min for $^{11}$C and 2.05 min for $^{15}$O), these tracers can only be used in centers with an in-house cyclotron. Moreover, the gaseous form of CO and the need for administration by inhalation necessitates sophisticated equipment for either human or animal studies.

Commercial availability of the species specific isoforms of albumin including human serum albumin (HSA) makes blood drawing unnecessary. In fact, $^{131}$I-labeled HSA is the only FDA approved radiologic agent for measuring blood volume. For imaging purpose, albumin has been labeled with various radioisotopes for PET imaging including $^{68}$Ga (Hoffend J. et al., *Nucl Med Biol*. 2005; 32(3): 287-292), $^{62}$Cu (Okazawa H. et al., *J Nucl Med* 1996; 37(7): 1080-1085), and $^{64}$Cu (Anderson C J et al., *Nucl Med Biol*. 1993; 20(4): 461-467). Compared with these radiometals, $^{18}$F has the advantages of being a pure positron emitter and having an ideal half-life. It is the dominant radioisotope used for PET imaging for both clinical applications and preclinical investigations.

As a protein, albumin can be labeled with $^{18}$F through reaction of N-succinimidyl 4-$^{18}$F-fluorobenzoate (SFB) with an amine group or N-[2-(4-$^{18}$F-fluorobenzamido)ethyl]maleimide (FBEM) on the thiol group. In one study, Wangler et al. prepared 4-(di-tert-butyl-$^{18}$F-fluorosilyl)benzenethiol ($^{18}$F-SiFASH) and coupled it directly to rat serum albumin (RSA) (Wangler B. et al., *Bioconjug Chem* 2009; 20(2): 317-321). However, high liver uptake was observed on the $^{18}$F-SiFA-RSA blood pool scan, indicating that the albumin structure may have been disrupted to some extent during labeling. One alternative is in vivo labeling of endogenous albumin with a pre-labeled albumin binder. Ideally, the binder will not affect the in vive behavior of the serum albumin such as circulation, extravascularization, and turnover; thus the imaging results will reflect the distribution and metabolism of serum albumin accurately. Currently available albumin binders include small molecules, peptides that possess an albumin binding domain, and antibodies.

Identification of liver lesions is of critical importance due to the increasing incidence of primary hepatic malignancies worldwide and an increase in detection of benign liver lesions by the widespread use of abdomen cross-sectional imaging modalities. Although many typical lesions can be detected by traditional imaging tests such as ultrasound, CT, and MRI, there remains a challenge to diagnose atypical lesions. For example, hypervascular neuroendocrine tumors often share the same appearance as hemangiomas on MRI. Some atypical hepatic cysts may also show overlapping features with hepatic metastasis from ovarian malignancies.

The lymphatic system plays a key role in maintaining tissue interstitial pressure by collecting protein-rich fluid that is extracted from capillaries. The lymphatic system is also a critical component of the immune system. Many types of malignant tumors such as breast cancer, melanoma, and prostate cancer are prone to metastasize to regional lymph nodes (LNs), possibly through tumor associated lymphatic channels. The status of these sentinel LNs (SLNs) not only provides a marker for tumor staging but also serves as an indicator of prognosis. Consequently, detection and mapping of SLNs is a key step in therapeutic decision-making (Veronesi U, et al., *Lancet* 1997, 349(9069): 1864-1867).

One common method used in the clinic is a two-step procedure which consists of local administration of radionuclide-labeled colloids, mostly with technetium-99m, several hours before the injection of a vital dye such as Patent blue (isosulfan blue). SLNs can be visualized either by gamma scintigraphy or SPECT (single photon emission computed tomography). The SLNs during surgery can be located with a hand-held gamma ray counter and visual contrast of the blue dye. However, this method requires separate administration of two agents because of different rates of local migration of the colloidal particles and blue dye molecules. Due to the relatively low sensitivity and poor spatial resolution of scintigraphy and SPECT, it is highly desirable to develop new imaging probes for other imaging modalities. The objective is to improve the detection of SLNs either for noninvasive visualization or intrasurgical guidance.

Recently, imaging guided surgery, especially with fluorescent probes, has been intensively studied due to its low cost, simplicity, and adaptability. The limited tissue penetration of light is less critical because of open field of view during surgery. For example, NIR fluorescence dyes, such as indocyanine green (ICG), have been investigated for sentinel node navigation during surgery either alone or in combination with nanoformulations (Hirano A, et al., *Ann Surg Oncol* 2012, 19(13):4112-4116; Koo J, et al., *Phys Med Biol* 2012, 57(23):7853-7862). Owing to the nanometer-scale size, stability and strong fluorescence, various nanoparticles and nanoformulations have been applied for SLN imaging and showed promising results in preclinical models. However, most of these probes are composed of heavy metals making their clinical translation difficult due to the acute and chronic toxicity. In addition, scattering and tissue attenuation cause poor results for pre-surgical evaluation of SLNs using optical imaging.

Thus, there remains a need in the art for improved methods for imaging of blood pools and the lymphatic system.

BRIEF SUMMARY OF THE INVENTION

The invention provides a compound of formula (T):

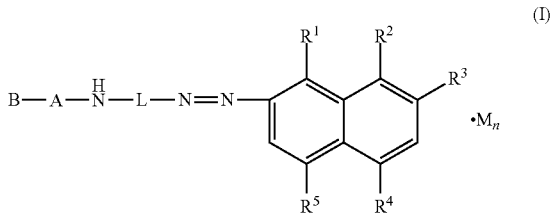

(I)

wherein L is a linker group selected from aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, wherein A is selected from a bond, C=O, and $C_1$-$C_6$ alkyl, wherein B is a chelating group selected from 1, 4, 7-triazacyclononane-N,N',N''-triacetic acid, 1, 4, 7,10-tetrazacyclononane-N,N',N''-triacetic acid, triethylenetetramine, diethylenetetramine pentaacetic acid, and hydrazinonicotinamide, wherein $R^1$-$R^5$ are independently selected from hydrogen, OH, $NH_2$, and $SO_3H$, wherein n is 0 or 1, and wherein M is selected from $^{18}F$-AlF, $^{60}Cu$, $^{61}Cu$, $^{62}Cu$, $^{64}Cu$, $^{67}Cu$, $^{68}Ga$, $^{86}Y$, $^{89}Zr$, $^{111}In$, $^{99m}Tc$, $^{186}Re$, $^{188}Re$, $Gd^{3+}$, and $Mn^{2+}$.

The invention also provides a method of blood-pool imaging in a mammal, comprising administering to the mammal a compound of formula (I):

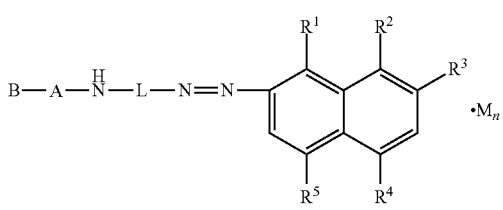

(I)

wherein L is a linker group selected from aryl, biaryl, heteroaryl, and biheteroaryl, wherein the aryl, biaryl, heteroaryl, or biheteroalyl is optionally substituted with one or more groups selected from alkyl, halo, hydroxy, and alkyloxy, wherein A is selected from a bond, C=O, and $C_1$-$C_6$ alkyl, wherein B is a chelating group selected from 1, 4, 7-triazacyclononane-N,N',N''-triacetic acid, 1, 4, 7,10-tetrazacyclononane-N,N',N''-triacetic acid, triethylenetetramine, diethylenetetramine pentaacetic acid, and hydrazinonicotinamide, wherein $R^1$-$R^5$ are independently selected from hydrogen, OH, $NH_2$, and $SO_3H$, wherein n is 0 or 1, and wherein M is selected from $^{18}F$-AlF, $^{60}Cu$, $^{61}Cu$, $^{62}Cu$, $^{64}Cu$, $^{67}Cu$, $^{68}Ga$, $^{86}Y$, $^{89}Zr$, $^{111}In$, $^{99m}Tc$, $^{186}Re$, $^{188}Re$, $Gd^{3+}$, and $Mn^{2+}$, and PET imaging the mammal.

The invention further provides a method of imaging a lymph node in a mammal, comprising administering to the mammal a compound of formula (I):

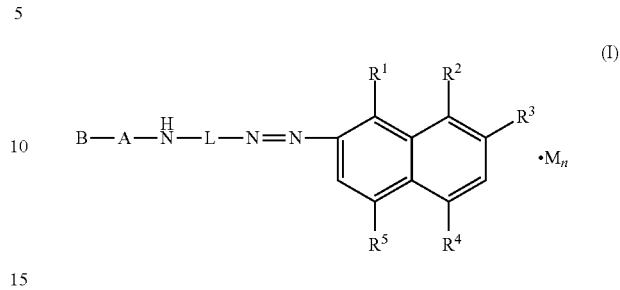

(I)

wherein L is a linker group selected from aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, wherein A is selected from a bond, C=O, and $C_1$-$C_6$ alkyl, wherein B is a chelating group selected from 1, 4, 7-triazacyclononane-N,N',N''-triacetic acid, 1, 4, 7,10-tetrazacyclononane-N,N',N''-triacetic acid, triethylenetetramine, diethylenetetramine pentaacetic acid, and hydrazinonicotinamide, wherein $R^1$-$R^5$ are independently selected from hydrogen, OH, $NH_2$, and $SO_3H$, wherein n is 0 or 1, and wherein M is selected from $^{18}F$-AlF, $^{60}Cu$, $^{61}Cu$, $^{62}Cu$, $^{64}Cu$, $^{67}Cu$, $^{68}Ga$, $^{86}Y$, $^{89}Zr$, $^{111}In$, $^{99m}Tc$, $^{186}Re$, $^{188}Re$, $Gd^{3+}$, and $Mn^{2+}$, and PET imaging the mammal.

The invention additionally provides a method of preparing a compound of formula (IV):

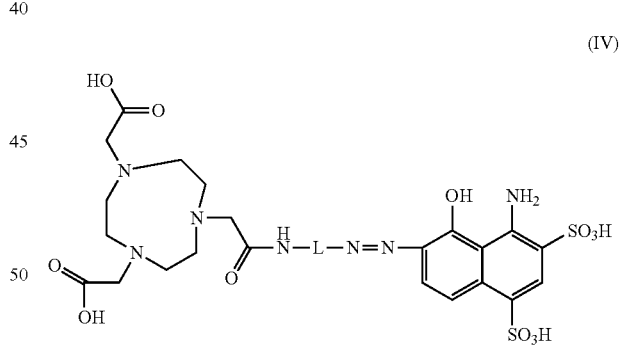

(IV)

wherein L is a linker group selected from aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, wherein M is selected from $^{18}F$-AlF, $^{64}Cu$, or $^{68}Ga$, and wherein n is 0 or 1, comprising the steps of:

(i) reacting a bis amino compound of the formula: $H_2N$-L-$NH_2$ wherein L is aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, with 1, 4, 7-triazacyclononane-N,N',N''-triacetic acid to form a compound of formula (II):

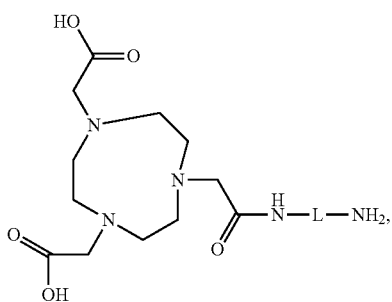

(iii) reacting the compound of formula (II) with a diazotization reagent to form a compound of formula (III):

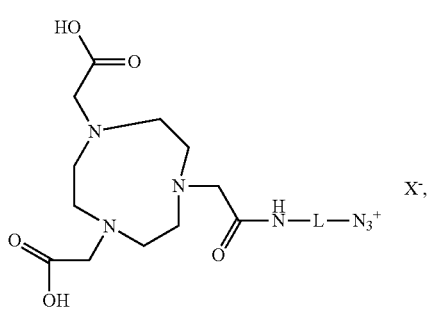

and (iv) reacting the compound of formula (III) with 4-amino-5-hydroxynaphthalene-1,3-disulfonic acid to form the compound of formula (IV).

BRIEF DESCRIPTION OF THE SEVERAL VIEWS OF THE DRAWING(S)

FIGS. 1A and 1B show the absorbance and fluorescence emission of Evans blue with and without albumin. Evans blue showed a strong absorbance peak at 620 nm with or without albumin. Evans blue is almost not fluorescent without albumin. However, with albumin, Evans blue showed a strong fluorescence emission peak at 680 nm.

Figure 3A:
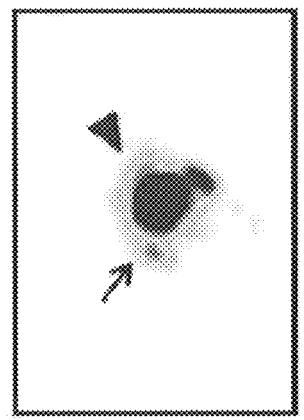
Figure 3B:
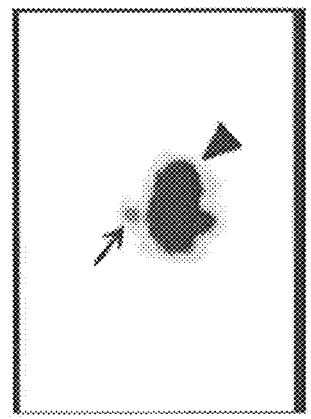
Figure 3C:
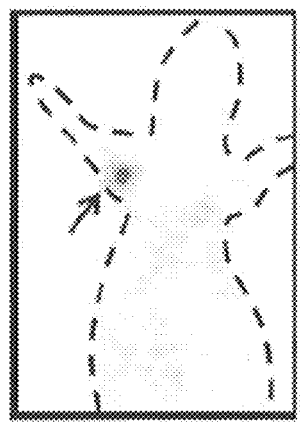

FIGS. 3A-3C show representative $^{18}$F-AlF-NEB PET images of an axillary LN in the orthotopic breast cancer model. FIG. 3A is a transaxial image, FIG. 3B is a sagittal image, and Figure C is a coronal image. PET scans were performed at 30 min after tracer injection. Arrows indicate tumor-draining axillary LNs and arrowheads indicate primary tumors. A dotted line was added to indicate animal contour.

Figure 3D:
Figure 3E:
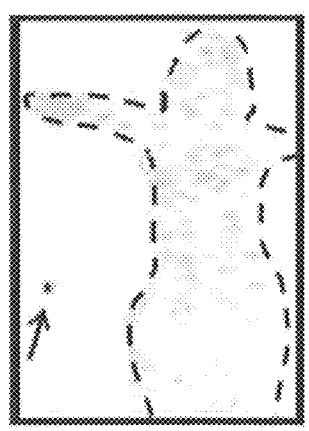

FIGS. 3D and 3E show confirmation of tracer uptake of an ipsilateral axillary LN after intratumoral injection of $^{18}$F-AlF-NEB.

Figure 3F:
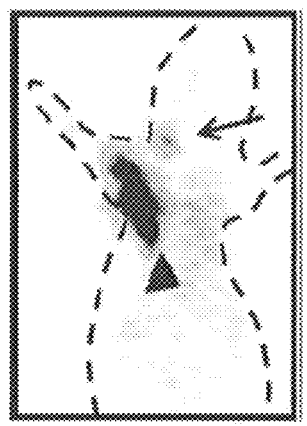

FIG. 3F shows a coronal image illustrating a cervical LN. Arrows indicate tumor-draining axillary LNs and arrowheads indicate primary tumors.

Figure 4:
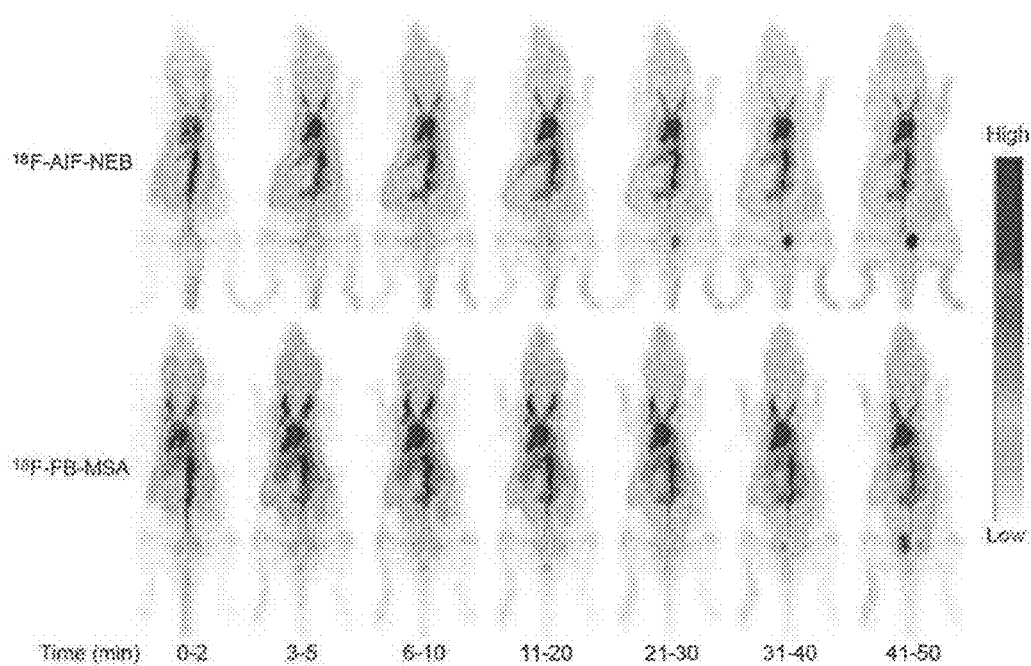

FIG. 4 shows a series of maximum-intensity-projection PET images in normal mice after intravenous injection of either $^{18}$F-AlF-NEB or $^{18}$F-FB-MSA. Each mouse received around 3.7 MBq of radioactivity. Images were reconstructed from a 60-min dynamic scan.

Figure 5A:
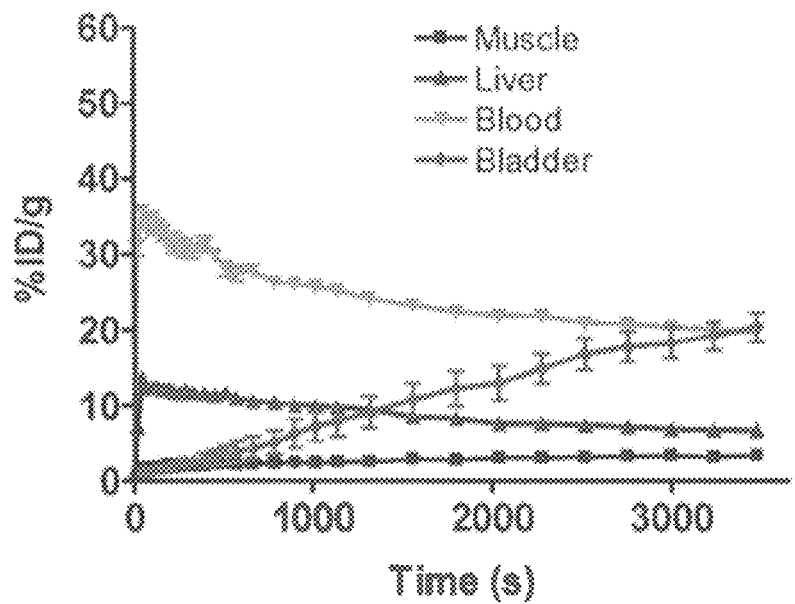

FIG. 5A shows time-activity curves of ROSs outlined over muscle, heart, liver, and bladder regions of $^{18}$F-AlF-NEB images.

Figure 5B:
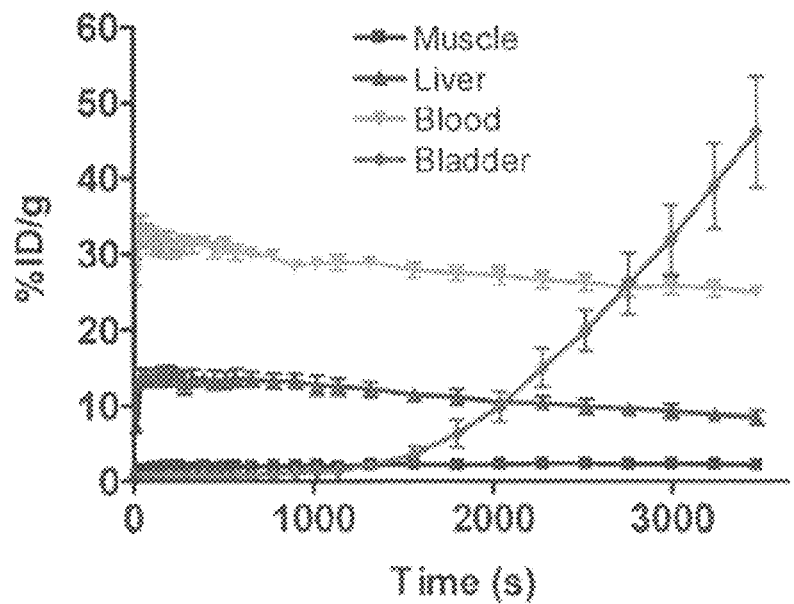

FIG. 5B shows time-activity curves of ROSs outlined over muscle, heart, liver, and bladder regions of $^{18}$F-FB-MSA images.

Figure 6:
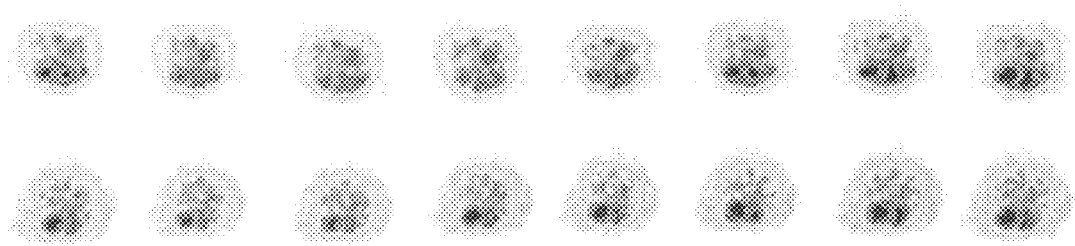

FIG. 6 shows ECG-gated blood-pool imaging of control and MI mice. Transaxial images were reconstructed to display 8 intervals of 1 cardiac cycle.

Figure 7A:
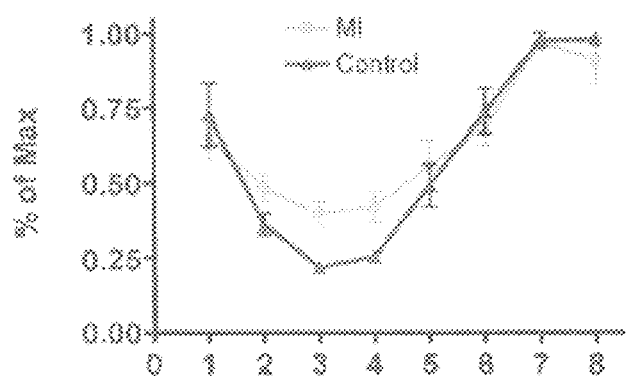

FIG. 7A show left ventricular volume curve calculated from PET.

Figure 7B:
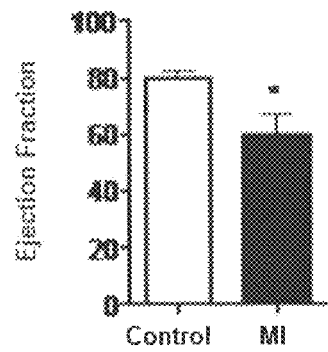

FIG. 7B shows left ventricular ejection fraction calculated from ECG-gated PET.

Figure 8:
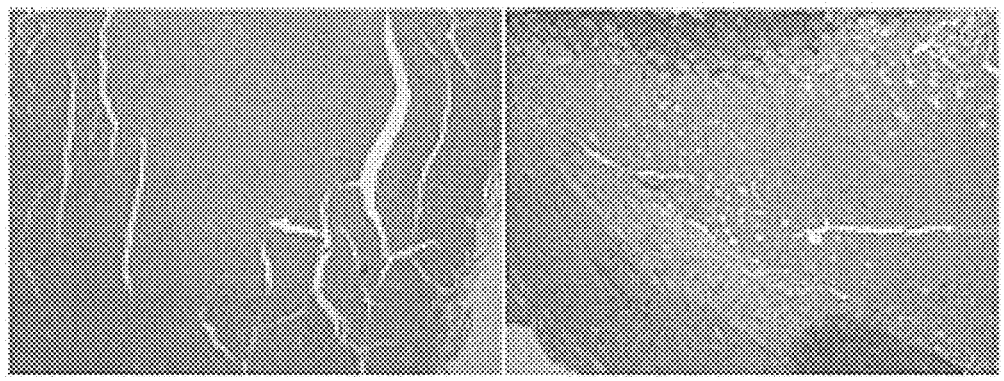

FIG. 8 shows hematoxylin and eosin staining of inflammatory muscles at 2 h after local injection of turpentine oil. Left panel: control. Right panel: inflammation.

Figure 9:
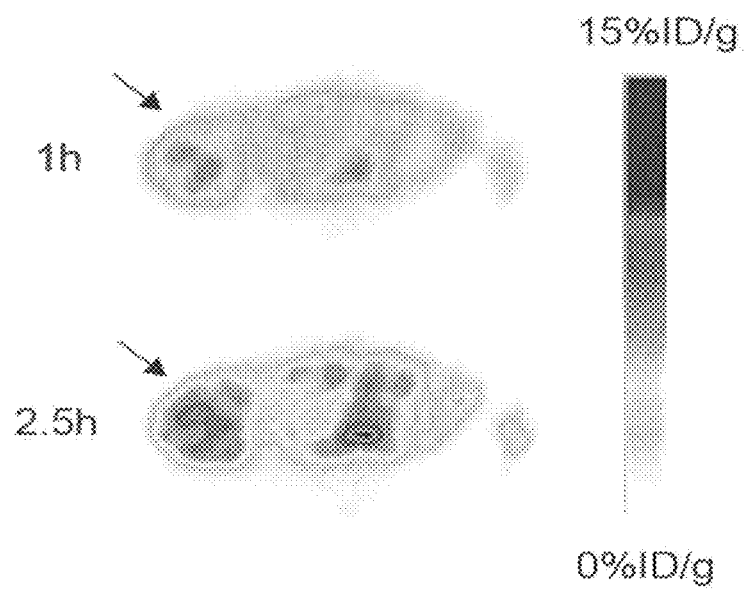

FIG. 9 shows transaxial PET images of mice that received turpentine oil infection. Ten-min static PET scans were obtained after intravenous injection of 3.7 MBq of $^{19}$F-AlF-NEB. Apparent radioactivity accumulation was observed in inflamed muscles at both 1 h (upper panel) and 2.5 h (lower panel) after tracer injection, as indicated by arrows.

Figure 10:
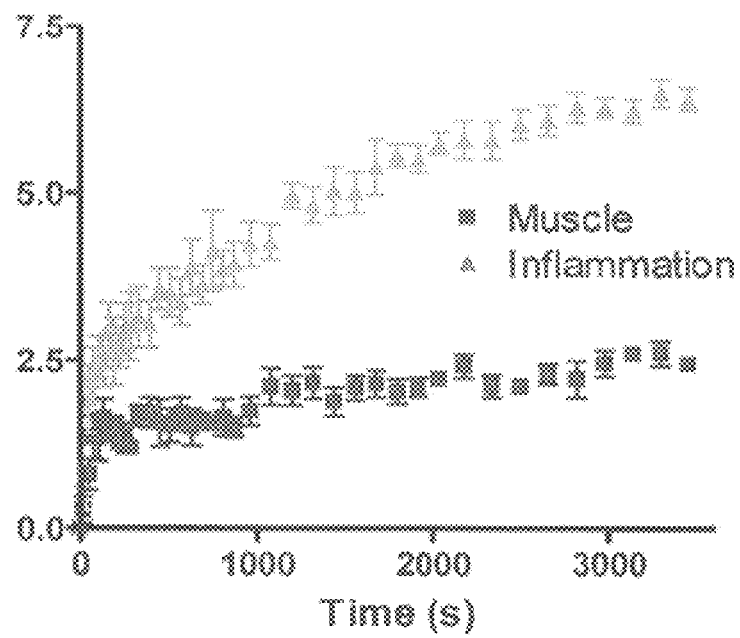

FIG. 10 shows time-activity curves over inflamed and contralateral healthy muscles based on PET images from a 60-min dynamic scan using $^{18}$F-AlF-NEB.

Figure 11:
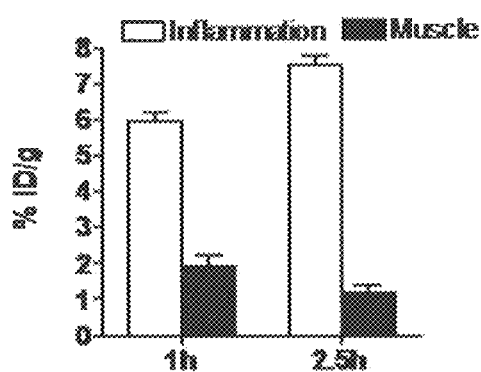

FIG. 11 shows quantitative analysis of $^{18}$F-AlF-NEB uptake in both inflamed and contralateral healthy muscles at 1 and 2.5 h after tracer injection.

Figure 12:
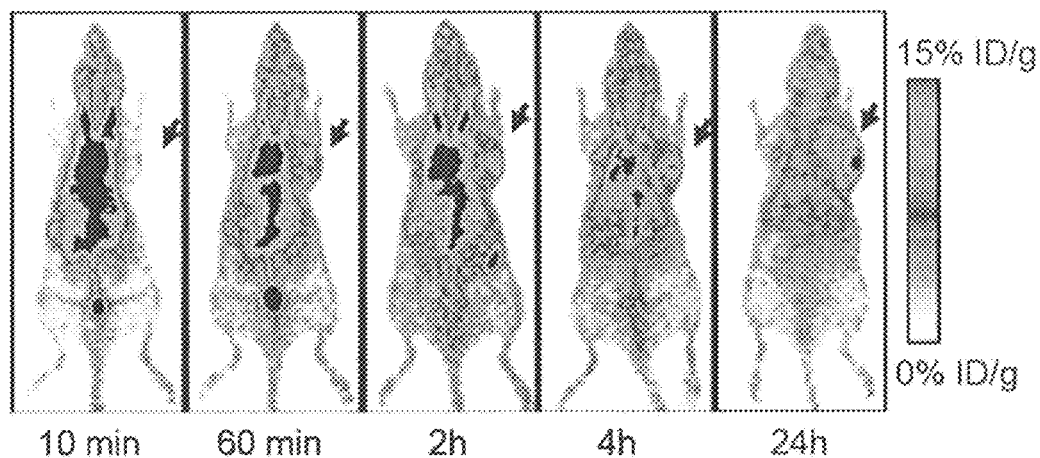

FIG. 12 shows a series of maximum-intensity-projection PET images of UM-tumor-bearing mice after intravenous injection of $^{64}$Cu-NEB. Tumors are indicated by arrows.

Figure 13:
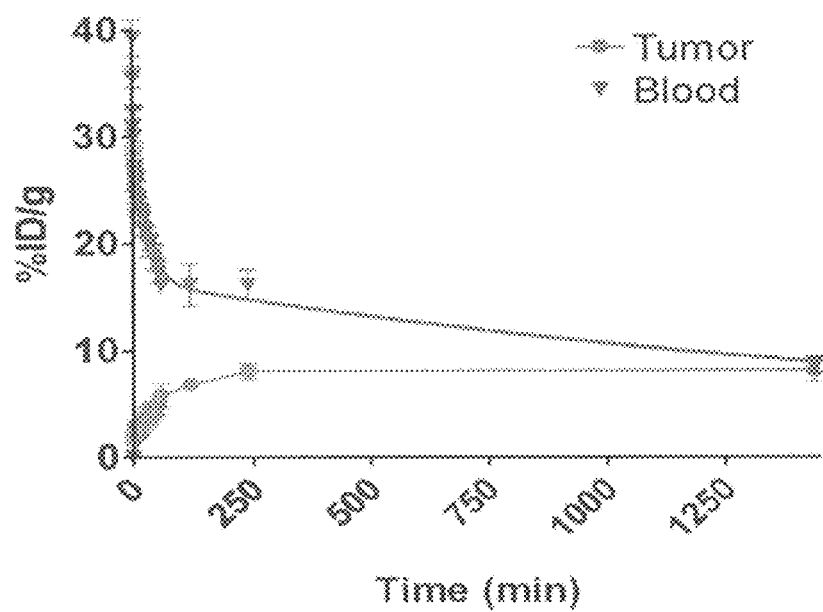

FIG. 13 shows time-activity curves of ROIs over heart and tumor regions.

Figure 14A:
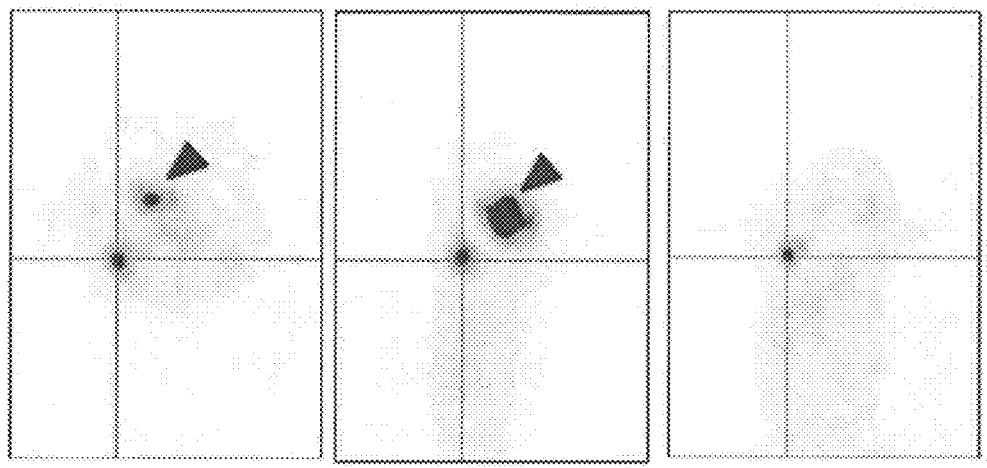

FIG. 14A shows representative $^{18}$F-AlF-NEB PET images of axillary LNs in the orthotopic breast cancer model (left panel: transaxial; middle panel: sagittal; right panel: coronal image). Arrowheads indicate primary tumors.

Figure 14B:
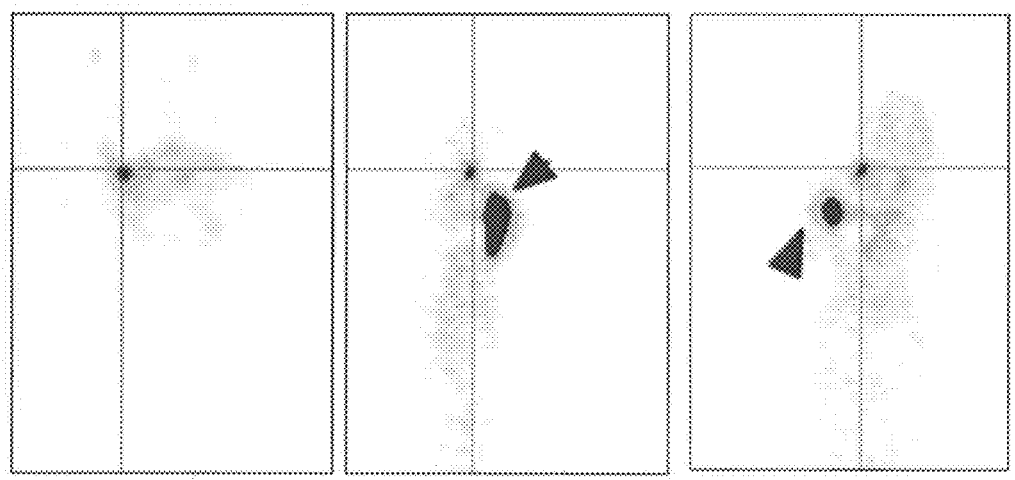

FIG. 14B shows representative $^{18}$F-AlF-NEB PET images of a cervical LH in the orthotopic breast cancer model (left panel: transaxial; middle panel: sagittal; right panel: coronal image). Arrowheads indicate primary tumors.

Figure 15A:
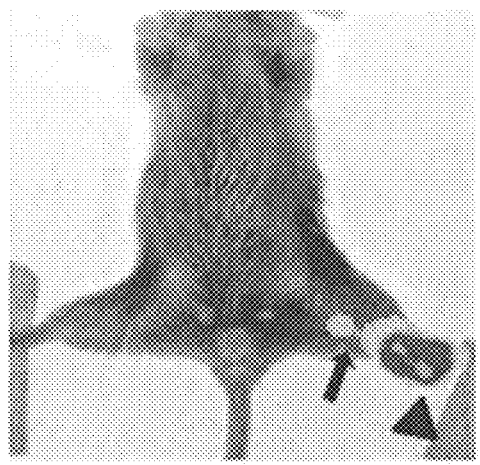

FIG. 15A shows representative BLI imaging of a metastatic popliteal LN (arrow) located near the primary tumor (arrowhead).

Figure 15B:
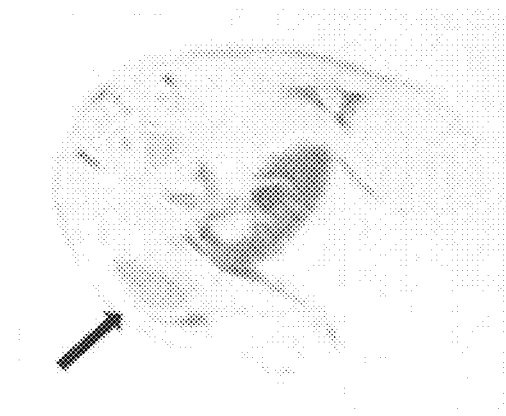

FIG. 15B shows axial $T_2$-weighted MRI of an enlarged metastatic popliteal LN as indicated by the arrow.

Figure 15C:
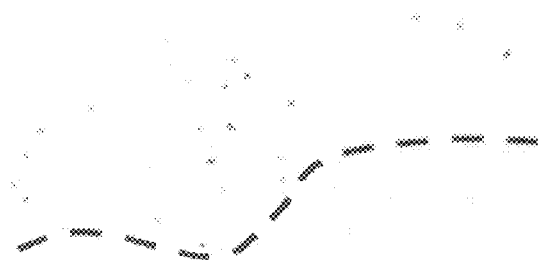

FIG. 15C shows confirmation of the existence of metastatis in the popliteal LN by imunofluorescence staining.

Figure 16:
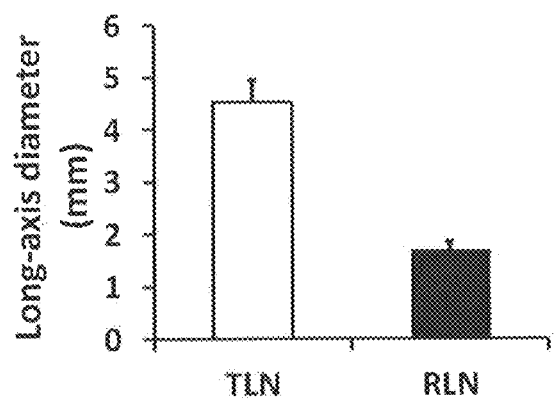

FIG. 16 shows that the average long-axis diameter of the left LN measured by MRI is significantly larger than that of the right one in the popliteal LN depicted in FIG. 15A.

Figure 17A:
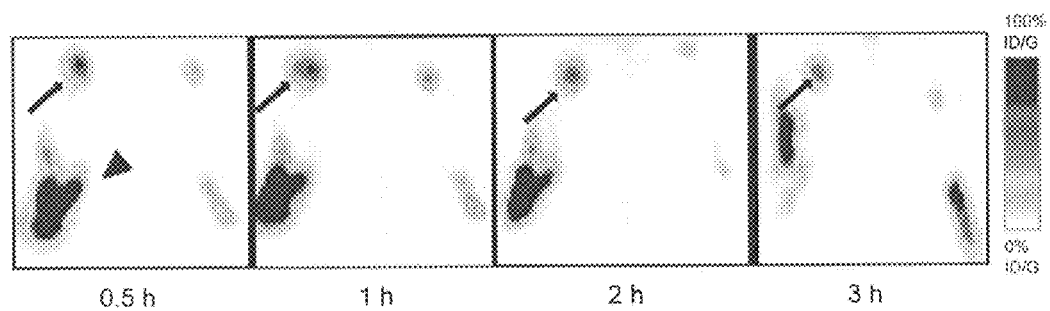

FIG. 17A shows representative coronal PET images of metastatic popliteal LNs (arrows) at different time points after local injection of $^{18}$F-AlF-NEB. Arrowheads indicate the injection site.

Figure 17B:
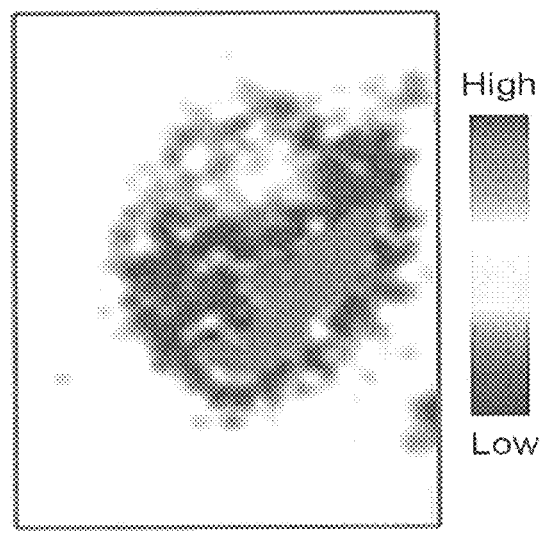

FIG. 17B shows autoradiography of the popliteal LN, confirming the metastasis (cold area in the LN).

Figure 17C:
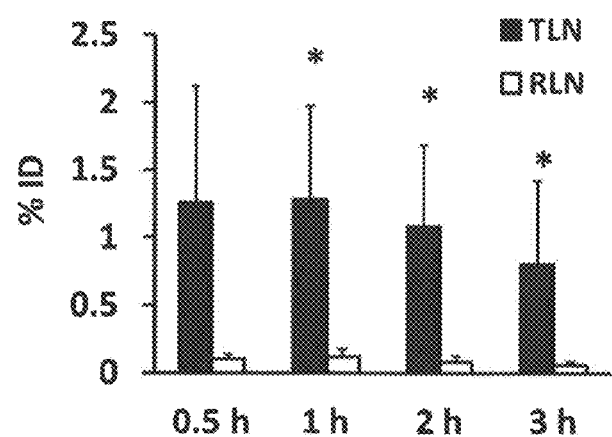

FIG. 17C shows the quantitative analysis of the total tracer uptake in tumor-draining LN (TLN) and right side normal LN (RLN). The value was corrected by the weights of LNs (*P<0.05).

Figure 18A:
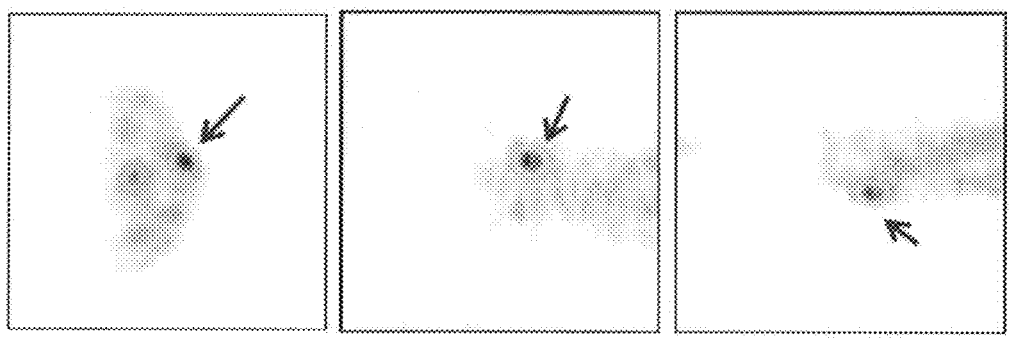

FIG. 18A depicts representative PET images which show high tracer uptake in sciatic LN. Left panel: transaxial; middle panel: coronal; right panel: sagittal.

Figure 18B:
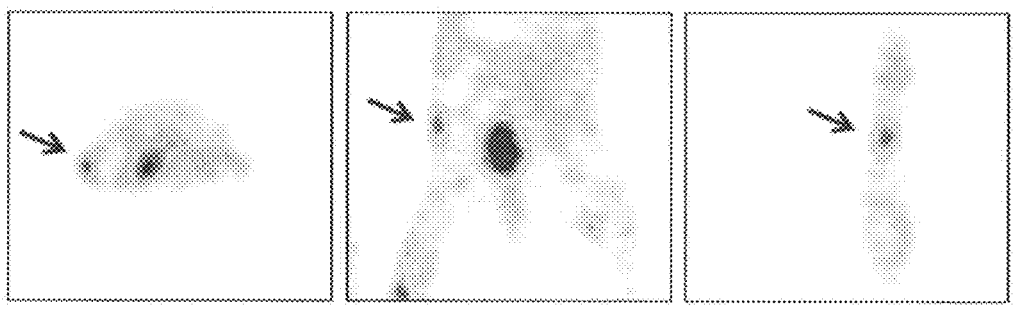

FIG. 18B depicts representative PET images which show high tracer uptake in inguinal LN. Left panel: transaxial; middle panel: coronal; right panel: sagittal.

FIG. 18C shows the H&E stain of a healthy popliteal LN.

FIG. 18D shows the H&E stain of a metastatic popliteal LN. The dashed line delineates metastasis foci at the subscapular sinus area.

FIGS. 18E and 18F show that H&E staining found micrometastasis foci inside two of the tumor-draining LNs at 4 weeks after inoculation of Fluc$^+$4T1 cells via hock injection.

Figure 19A:
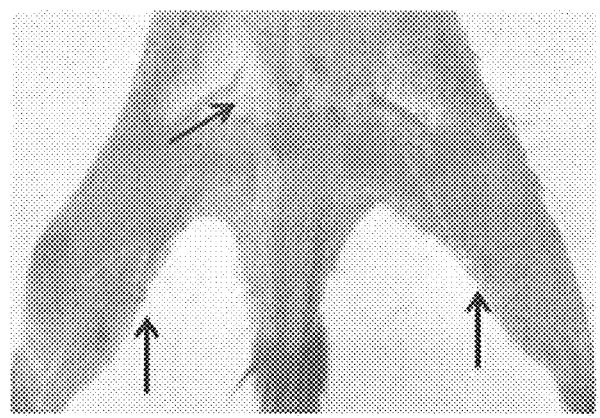

FIG. 19A shows LN mapping with Evans blue dye in a turpentine oil-induced hind limb inflammation model. The lower two arrows indicate popliteal LNs and the upper arrow shows the left sciatic LN.

Figure 19B:
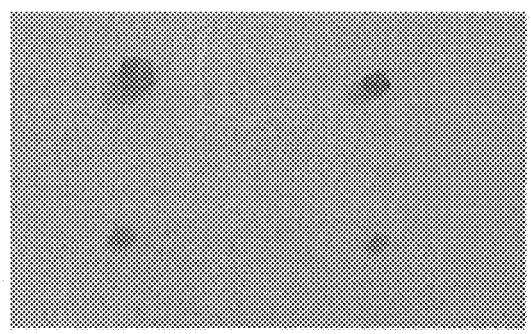

FIG. 19B shows a photograph of excised LNs. The upper two are popliteal LNs, and the lower two are sciatic LNs. LNs on the left side are harvested from the inflamed hind limb, whereas those on the right side are from a normal limb.

Figure 20:
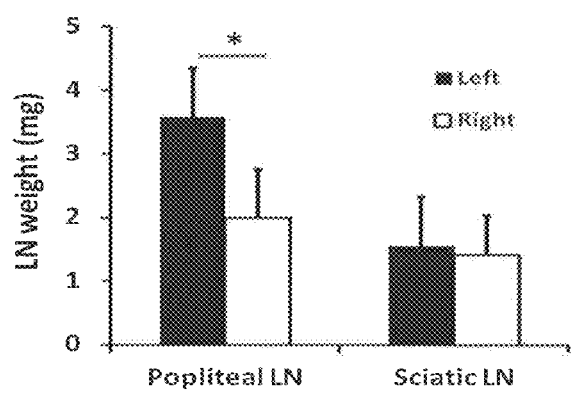

FIG. 20 shows a quantitative analysis of LN size based on its weight (*P<0.05).

Figure 21:
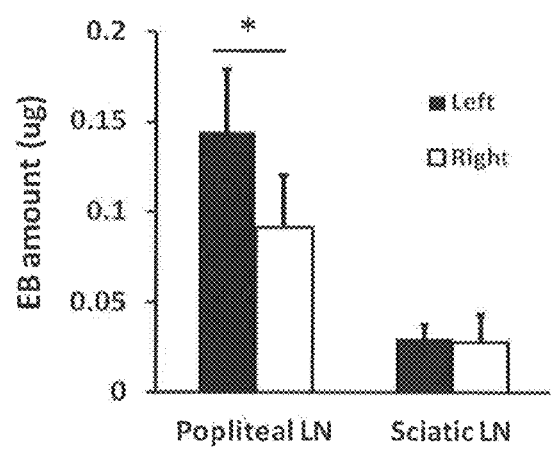

FIG. 21 depicts the measurement of UV showing the difference of Evans blue dye in different LNs (*P<0.05).

Figure 22:
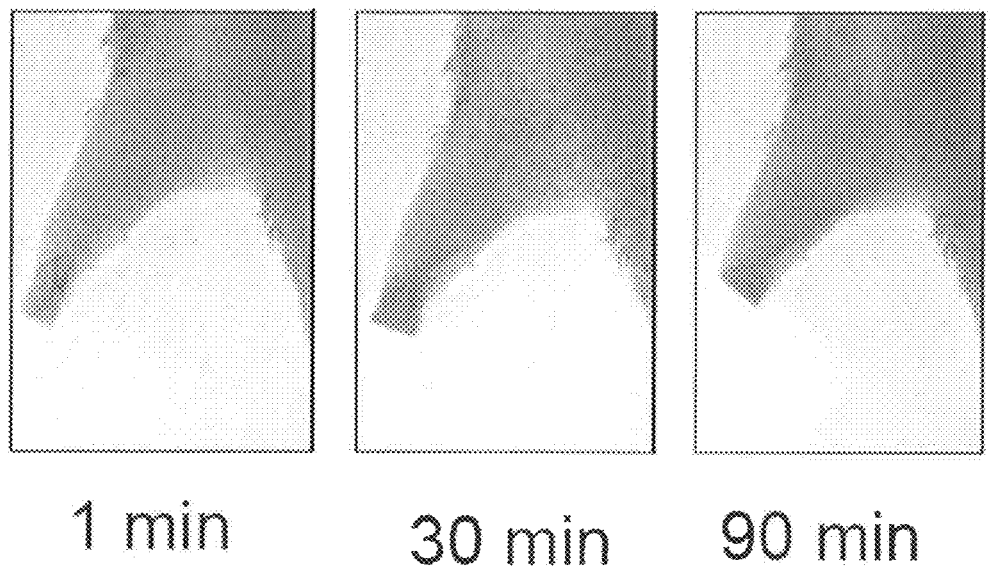

FIG. 22 shows longitudinal fluorescence imaging of the lymphatic system after hock injection of $^{18}$F-AlFNEB/EB. LNs and lymphatic vessels can be clearly seen with the migration of the tracer along with time.

Figure 23A:

FIG. 23A shows ex vivo optical imaging of LNs without skin.

Figure 23B:

FIG. 23B shows a photograph of the same mice to show the blue color (shown in black) of the LNs.

Figure 24A:
Figure 24A:
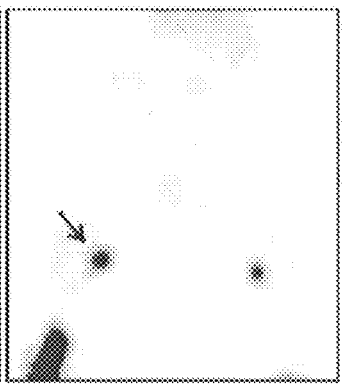
Figure 24A:

FIG. 24A shows coregistration of optical image (left panel) and PET image (middle panel) with the overlay shown in the right panel. Popliteal LNs are indicated by the arrow.

Figure 24B:
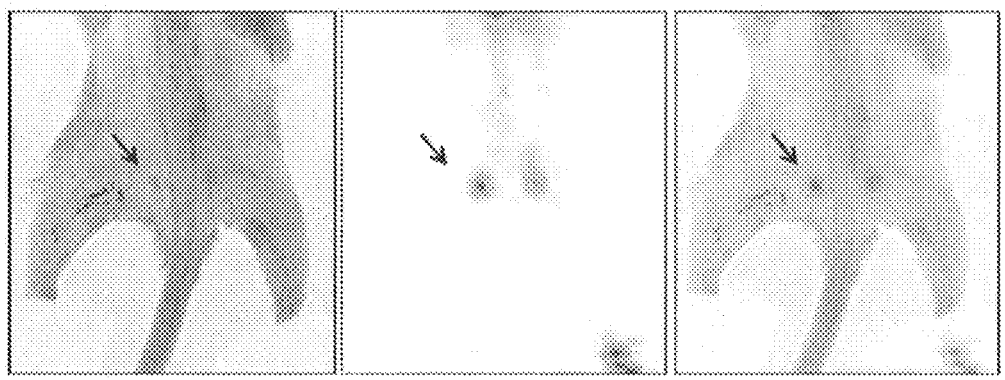

FIG. 24B shows coregistration of optical image (left panel) and PET image (middle panel) with the overlay shown in the right panel. Sciatic LNs are indicated by the arrow.

Figure 25:
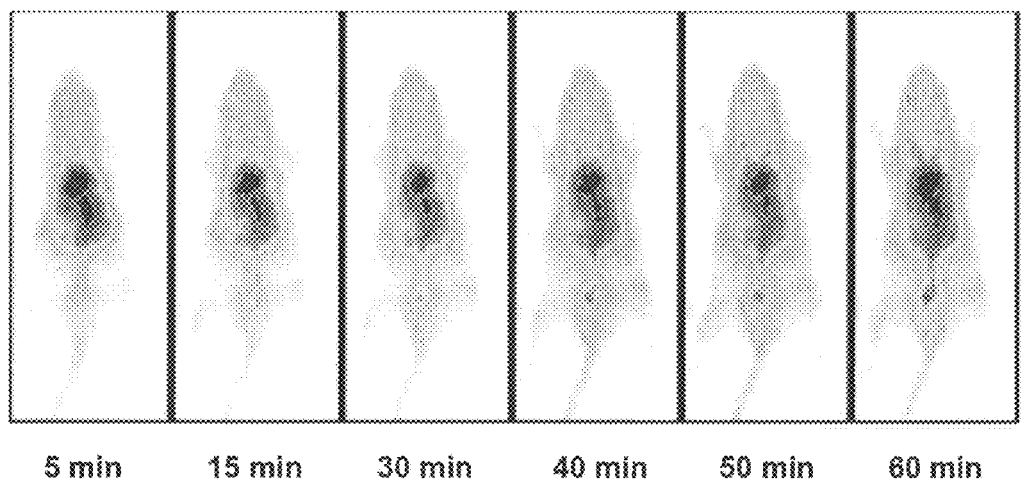

FIG. 25 shows a representative coronal maximum intensity projection of PET images of 60 dynamic acquisitions. For dynamic PET scans, four BALB/C mice was injected intravenously with 1.85 MBq (50 µCi) of $^{68}$Ga-NEB under isoflurane anesthesia. A 60 min list mode acquisition was performed with an Inveon PET scanner. Image reconstruction was done by the 2-dimensional ordered subsets expectation maximum (OSEM) algorithm without attenuation or scatter correction.

Figure 26:
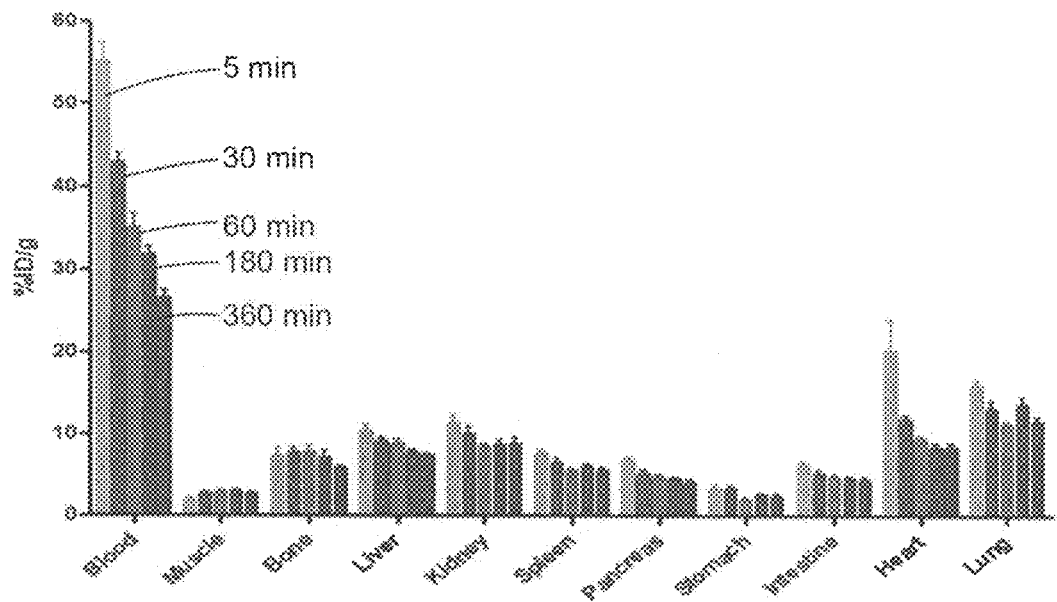

FIG. 26 shows decay corrected biodistribution of $^{68}$Ga-NEB in normal Balb/c mice (n=5/group).

Figure 27A:
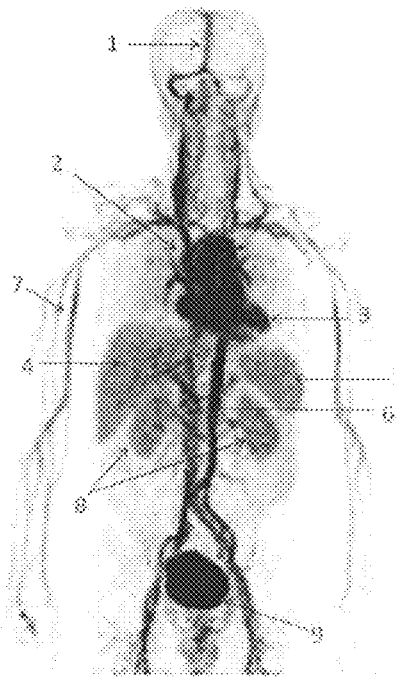

FIG. 27A shows coronal maximum intensity projection (MIP) in a male volunteer. The PET image was acquired at 30 min after intravenous administration of 3.75 mCi of $^{68}$Ga-NEB. Principal organs and regions of uptake are labeled: superior sagittal sinus (1), arch of aorta (2), cardiac ventricles (3), liver (4), spleen (5), abdominal aorta (6), limb vessels (7), kidneys and (8), bladder (9).

Figure 27B:
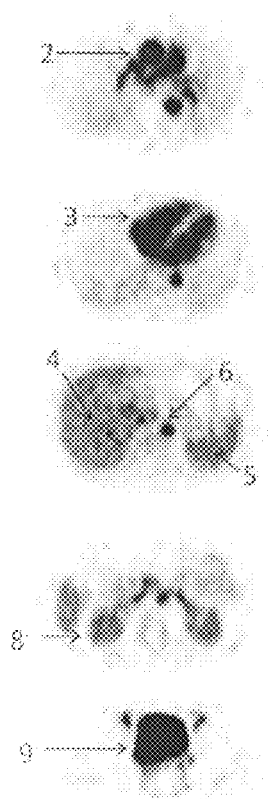

FIG. 27B shows corresponding axial PET and PET/CT fusion images at key levels to reflect arch of aorta, cardiac ventricles, liver and spleen, kidneys and bladder.

Figure 28:
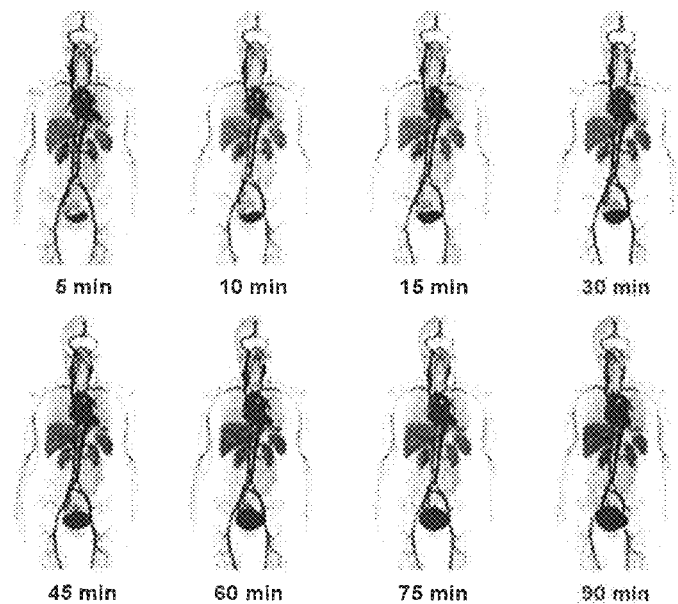

FIG. 28 shows multiple time point whole-body maximum intensity projection PET images of a healthy 52-year-old woman volunteer at 5, 10, 15, 30, 45, 60, 75, and 90 min after intravenous administration of $^{68}$Ga-NEB.

FIGS. 29A-29H show $^{68}$Ga-NEB PET of a patient with multiple hemangiomas. The lesion located in the left lobe was discerned on the whole body MIP of PET (29A). Different lesions of hemangioma were pointed out by arrows while the abdominal aorta was pointed out by triangle (29B-29H).

FIG. 30 shows images of hepatic hemangioma: v $^{68}$Ga-NEB PET/CT (A) shows strong local accumulation of radioactivity with the hepatic nodule, while $^{18}$F-FDG PET/CT (B) shows relatively low local uptake. vThe nodule is also identified by CT (C) without much signal contrast. v(D-F) Images of hepatic carcinoma.v The lesion shows negative contrast compared with surrounding normal hepatic tissue on $^{68}$Ga-NEB PET/CT (D) while increased FDG uptake is observed with $^{18}$F-FDG PET/CT (E).v (G-I) A case of neuroendocrine tumor (NET) liver metastases.v Multiple liver nodules are detected on CT scan (I).v $^{68}$Ga-NEB PET/CT (G) shows low uptake in all the hepatic nodules, compared with mild to moderate uptake in $^{18}$F-FDG PET/CT (H).

FIG. 31A-31C show $^{68}$Ga-NEB PET of a patient hepatocellular carcinoma. A case of hepatocellular carcinoma presented by whole body MIP of PET (A), transaxial CT (B) and $^{68}$Ga-NEB PET/CT (C). $^{68}$Ga-NEB PET showed decreased accumulation of radioactivity within the hepatic nodule.

DETAILED DESCRIPTION OF THE INVENTION

The invention provides a compound of formula (I):

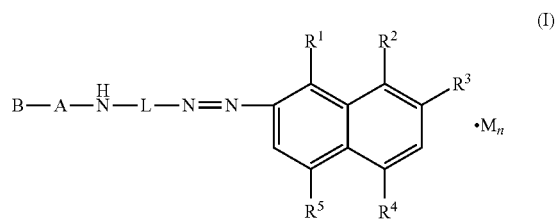

wherein L is a linker group selected from aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, wherein A is selected from a bond, C=O, and $C_1$-$C_6$ alkyl, wherein B is a chelating group selected from 1, 4, 7-triazacyclononane-N,N',N"-triacetic acid, 1, 4, 7,10-tetrazacyclononane-N,N',N"-triacetic acid, triethylenetetramine, diethylenetetramine pentaacetic acid, and hydrazinonicotinamide, wherein $R^1$-$R^5$ are independently selected from hydrogen, OH, $NH_2$, and $SO_3H$, wherein n is 0 or 1, and wherein M is selected from $^{18}$F-AlF, $^{60}$Cu, $^{61}$Cu, $^{62}$Cu, $^{64}$Cu, $^{67}$Cu, $^{68}$Ga, $^{86}$Y, $^{89}$Zr, $^{111}$In, $^{99m}$Tc, $^{186}$Re, $^{188}$Re, $Gd^{3+}$, and $Mn^{2+}$.

In an embodiment, L is biphenyl, optionally substituted with one or more groups selected from alkyl, halo, hydroxy, and alkyloxy.

In an embodiment, A is a bond.

In an embodiment, B is 1, 4, 7-triazacyclononane-N,N', N''-triacetic acid.

In a preferred embodiment, the compound of formula (I) is:

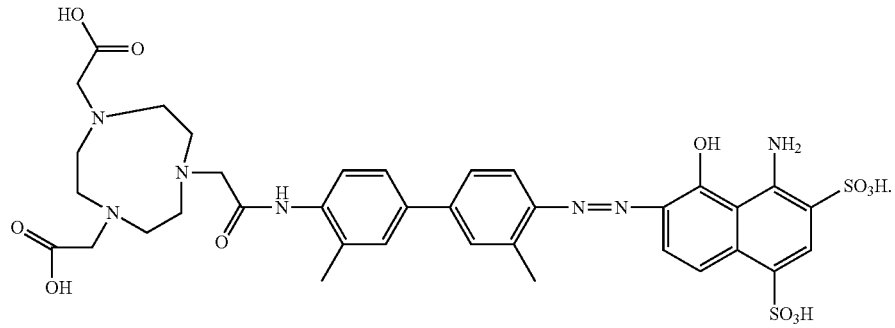 [SMILES: Cc1cc(-c2ccc(NC(=O)CN3CCN(CC(=O)O)CCN(CC(=O)O)CC3)c(C)c2)ccc1N=Nc1ccc2c(S(=O)(=O)O)cc(S(=O)(=O)O)c(N)c2c1O]

In a preferred embodiment, n is 1 and M is $^{18}$F-AlF, $^{64}$Cu, or $^{68}$Ga.

In a preferred embodiment, the compound of formula (I) is:

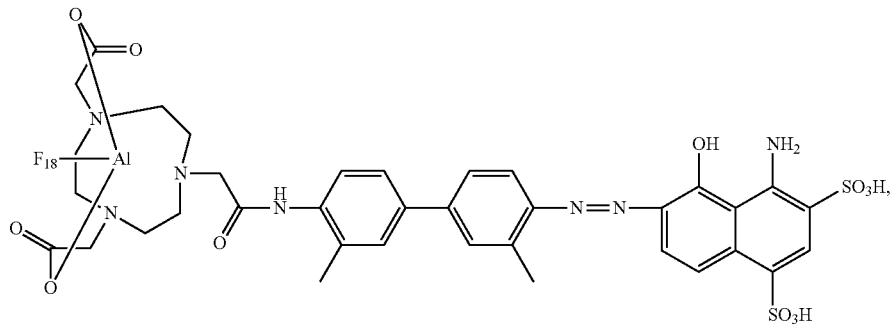

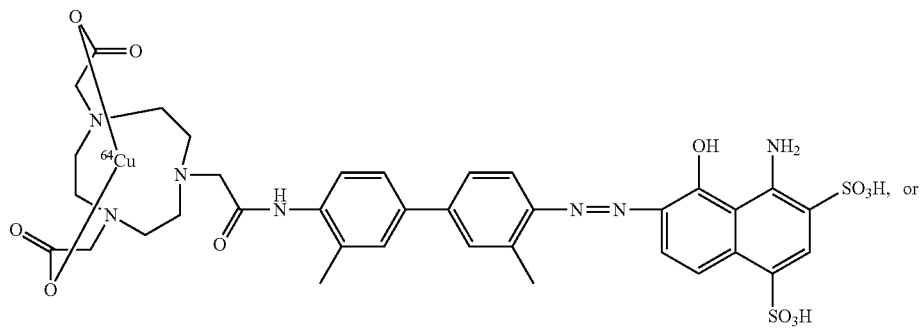

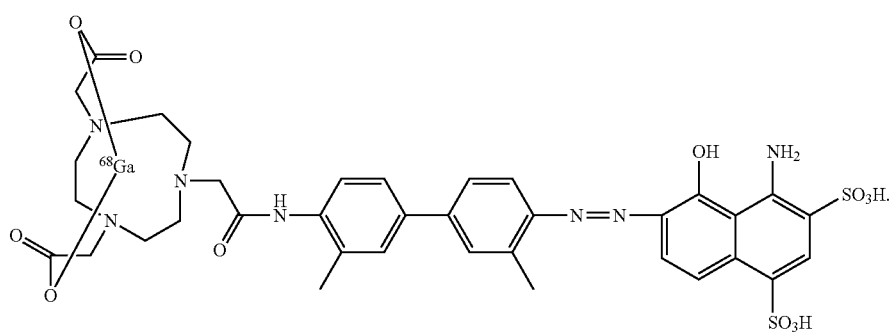

M can be any suitable diagnostic or therapeutic metal. Non-limiting examples of suitable diagnostic and therapeutic metals include paramagnetic metal ions, gamma-emitting radioisotopes, positron-emitting radioisotopes, and x-ray absorbers. Non-limiting examples of suitable paramagnetic metal ions include Gd(III), Dy(III), Fe(III), and Mn(III). Non-limiting examples of suitable gamma-emitting radioisotopes or positron-emitting radioisotopes include $^{60}$Cu, $^{61}$Cu, $^{62}$Cu, $^{64}$Cu, $^{67}$Cu, $^{68}$Ga, $^{99m}$Tc, $^{95}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, and $^{213}$Bi. Non-limiting examples of suitable x-ray absorbers include Re, Sm, Ho, Lu, Pm, Y, Bi, Pd, Gd, La, Au, Yb, Dy, Cu, Rh, Ag, and Ir. Preferably, M is selected from $^{18}$F-AlF, $^{60}$Cu, $^{61}$Cu, $^{62}$Cu, $^{64}$Cu, $^{67}$Cu, $^{68}$Ga, $^{86}$Y, $^{89}$Zr, $^{111}$In, $^{99m}$Tc, $^{186}$Re, $^{188}$Re, Gd$^{3+}$, and Mn$^{2+}$. More preferably, M is $^{18}$F-AlF, $^{64}$Cu, or $^{68}$Ga.

The compound of formula (I) can be prepared using any suitable method. In an embodiment, the compound of formula (I) is prepared by a method comprising the steps of:

(i) reacting a bis amino compound of the formula: H$_2$N-L-NH$_2$ wherein L is aryl, biaryl, heteroaryl, and biheteroaryl, wherein the aryl, biaryl, heteroaryl, or biheteroaryl is optionally substituted with one or more groups selected from alkyl, halo, hydroxy, and alkyloxy, with 1, 4, 7-triazacyclononane-N,N',N''-triacetic acid to form a compound of formula (II):

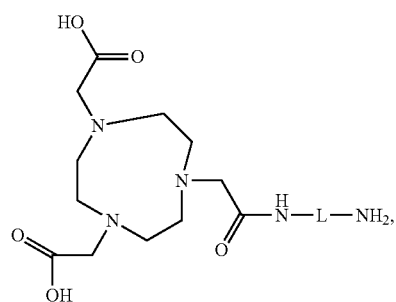

(iii) reacting the compound of formula (II) with a diazotization reagent to form a compound of formula (III):

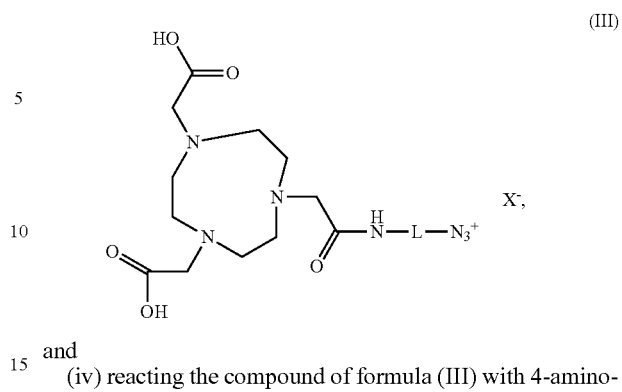

and (iv) reacting the compound of formula (III) with 4-amino-5-hydroxynaphthalene-1,3-disulfonic acid to form a compound of formula (IV):

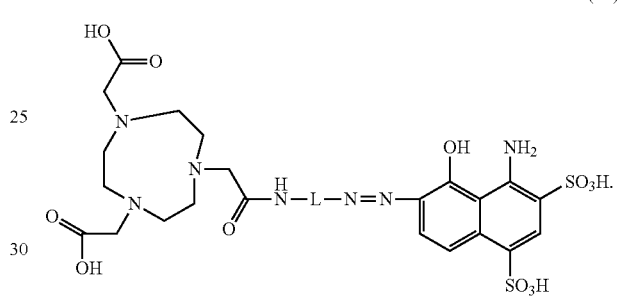

In an embodiment, the method further comprises a step of reacting the compound of formula (IV) with MX$_2$, wherein M is selected from $^{18}$F-AlF, $^{64}$Cu, or $^{68}$Ga and wherein X is a halogen, to provide a compound of formula (V):

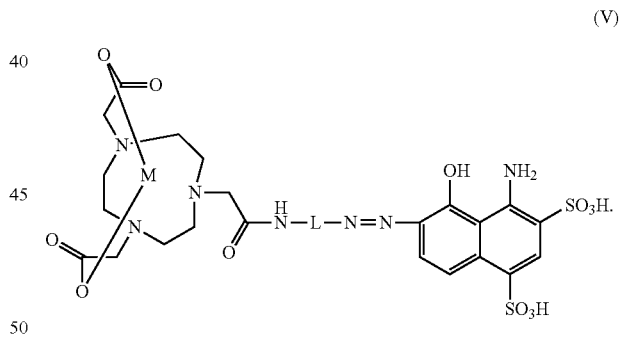

In a preferred embodiment, the compound of formula (V) is:

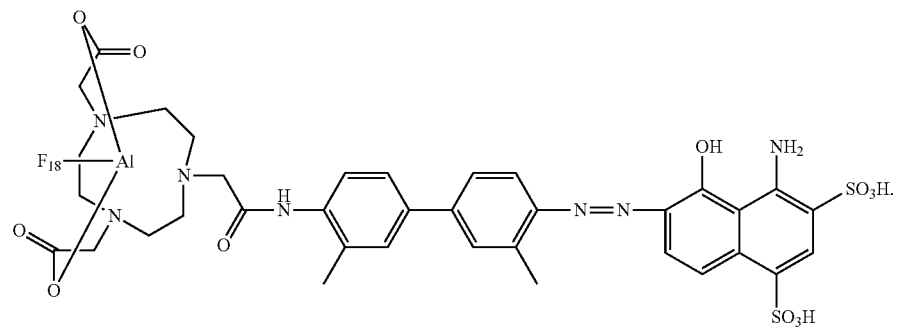

In another preferred embodiment, the compound of formula (V) is:

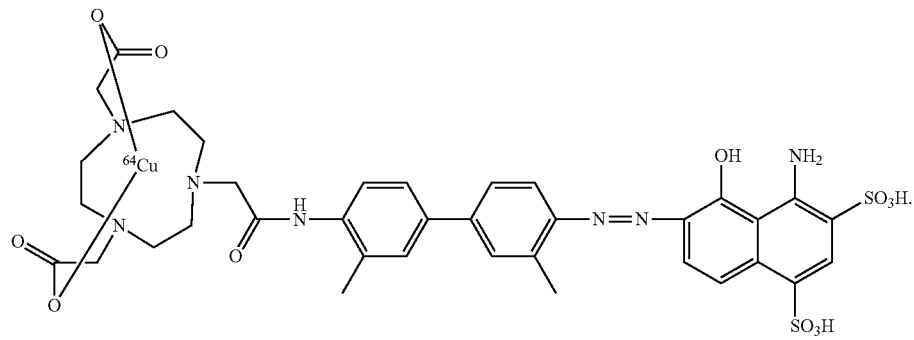

In another preferred embodiment, the compound of formula (V) is:

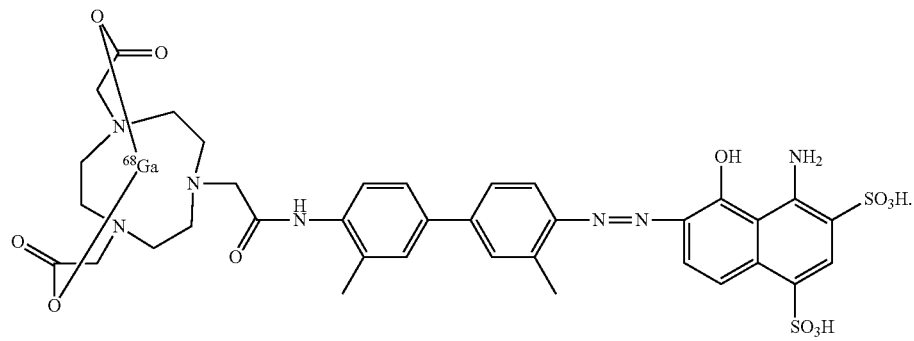

In a particular embodiment, the compound of formula (I) (also referred to herein as "NEB") wherein n is 0 can be synthesized in two steps starting from o-tolidine as shown in Scheme 1. 1, 4, 7-triazacyclononane-N,N,N"-triacetic acid-3HCl ("NOTA") was first coupled to o-tolidine using diethyl cyanophosphonate to give NOTA-o-tolidine in 26% yield after preparative reversed-phase HPLC. NOTA-o-tolidine was then coupled to 1-amino-8-naphthol-2,4-disulfonic acid to give NEB through the formation of diazonium salt with a yield of 46.6%. The purity of the product was >98% based on HPLC analysis and the identity of the product was confirmed by LC-MS. This truncated version of Evans blue retained the binding ability with albumin since stable NEB/albumin complex was confirmed by LC/MS. The complex formation was also confirmed by saturation binding assay. The bound NEB could be separated from the unbound NEB using agarose gel electrophoresis. Quantitation of the mass of unbound NEB as a function of its concentration allowed determination of the dissociation constant ($K_d$, 48.9±3.81 μM). The $^{18}$F-AlF complex of NEB is also referred to herein as $^{18}$F-AlF-NEB. The $^{64}$CU complex of NEB is also referred to herein as $^{64}$Cu-NEB.

The procedure for synthesis of the compound of formula (I) and its radiolabeling is shown in Scheme 1. The radiochemical yield for $^{18}$F-AlF-NEB was 58.4±11.3% (n=5) with a total synthesis and work-up time of 20-30 min. A single peak was detected on TLC and the radiochemical purity was >95% based on HPLC analysis (Supplementary FIGS. 3 and 4). Labeling of NEB with $^{64}$Cu also took 20-30 min with a radiochemical yield of 74%. For in vitro labeling of albumin, $^{18}$F-SFB was first prepared and purified by HPLC and then used for protein labeling. The whole labeling process took about 2-3 h with a radiochemical purity >95%. Both $^{18}$F-AlF-NEB and $^{64}$Cu-NEB showed very good stability in mouse serum even after 120 min incubation at 37° C.

Scheme 1

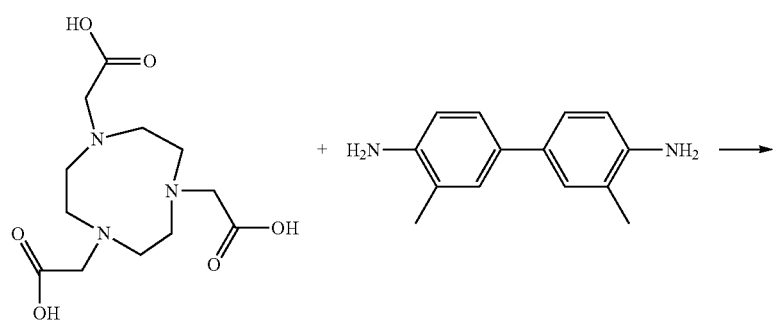

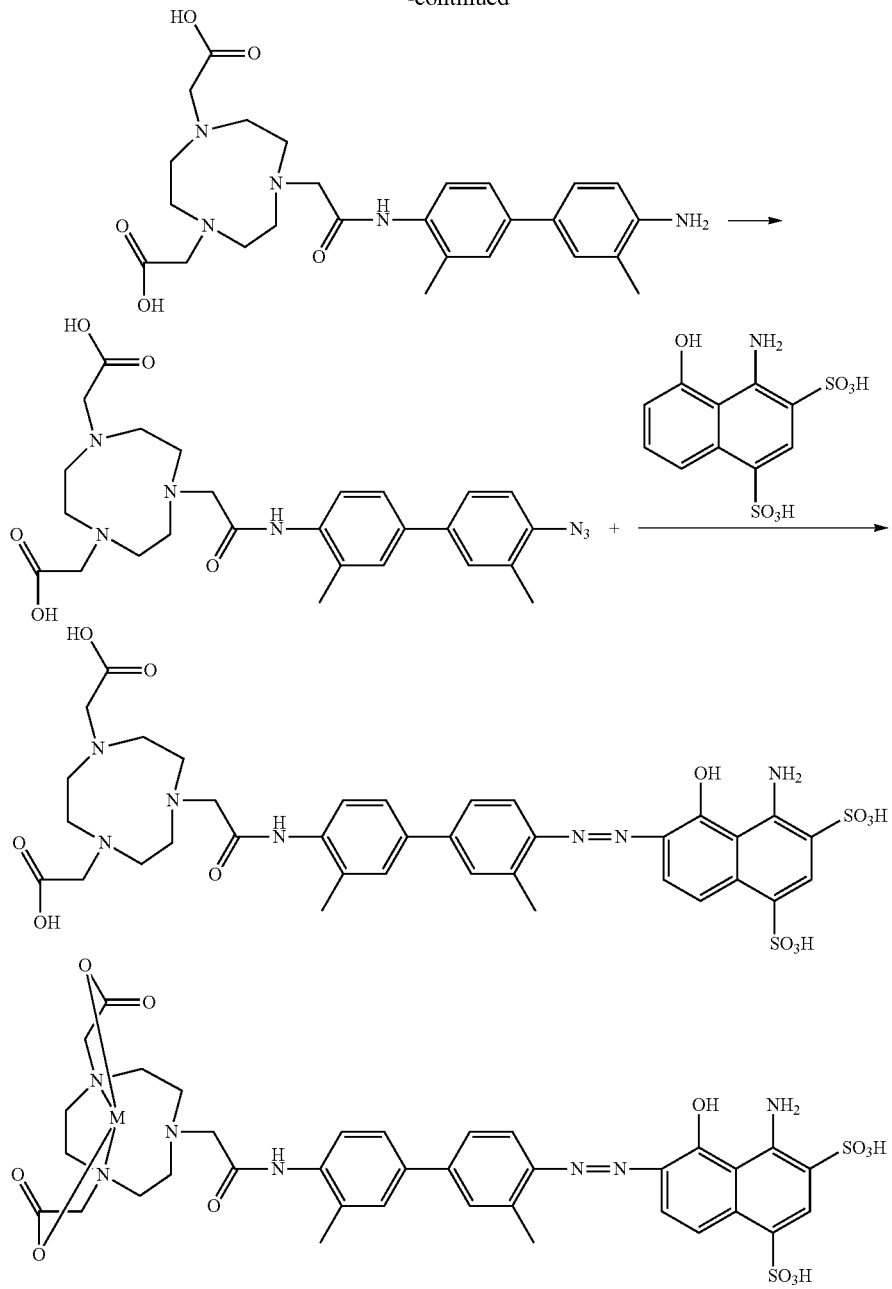

The compound of the invention can be used for imaging using any suitable imaging method. Non-limiting examples of suitable imaging methods include magnetic resonance imaging, single photon emission imaging, and positron emission tomographic imaging (PET). In a preferred embodiment, the imaging method is PET.

To meet the requirement for both clinical application and preclinical research, herein, a fast in vivo albumin labeling method for PET imaging was investigated. The preparation procedure is rapid and efficient. PET images using in vivo labeled albumin through a newly developed truncated Evans blue derivative $^{18}$F-AlF-NEB are comparable to those using in vitro labeled albumin through $^{18}$F-FB-Albumin. The in vivo labeling strategy can be applied to blood pool imaging to evaluate cardiac function under both physiological and pathological conditions. This method can also be used to evaluate vascular permeability in tumors, inflammatory diseases, and ischemic/infarcted lesions. Due to the simple synthesis procedure, this PET tracer has great potential for clinical translation. $^{18}$F-AlF-NEB is expected to be an ideal alternative to radiolabeled RBCs for blood pool imaging since autologous blood products present significant risks to both the operator handling the product and the patient receiving it.

As expected, a majority of the radioactivity was retained in the circulatory system after intravenous injection of $^{18}$F-AlF-NEB, which justifies the feasibility of using this tracer as a blood pool imaging agent. It is of note that immediately after intravenous injection of $^{18}$F-AlF-NEB, a small amount of tracer was rapidly cleared out of circulation before binding to albumin. The possibility of dissociation of NEB/albumin complex, cannot be excluded, especially at the early phase, since the dissociation constant of NEB to albumin is approximately 50 μM. However, due to the very low amount of NEB injected and highly abundant reservoir of albumin protein, the complex formation and its stability in the blood circulation is not of concern. Indeed, from 15 min to 60 min p.i., the tracer showed a much slower clearance of radioactivity from the blood. It is believed that this downward slope was caused mainly by the turnover of albumin from blood circulation to the interstitial space.

As the most widely used FDA approved PET imaging probe, $^{18}$F-FDG has been used for ECG gated PET imaging to evaluate cardiac function (Porenta G. et al., *J Nucl Med.* 1995; 36(6): 1123-1129). The parameters from FDG PET are comparable with those from MRI and CT studies. However, blood pool imaging probe such as $^{68}$Ga-DOTA-albumin has shown advantages over FDG PET because in the infarcted heart, the cardiac wall is not intact due to decreased or null uptake of FDG, leading to imprecise delineation of the infarcted myocardium. In this study, the cardiac ventricles and major vessels were successfully visualized by using $^{18}$F-AlF-NEB PET. After dividing each cardiac cycle into eight equal time intervals, the volume of left ventricle in each interval can be quantified to calculate the ejection fraction. Due to the limitation of spatial resolution and partial volume effect, the EFLV in MI mice based on PET quantification is higher than that from ultrasound. Besides, the accuracy of ECG gated PET imaging is also affected by the reconstruction algorithm, the software used for outlining ROIs and ECG gating.

$^{18}$F-AlF-NEB was applied to evaluate increased vascular permeability in both turpentine induced acute inflammation and xenografted tumor models. The inflamed muscle showed continuously increased radioactivity accumulation, indicating the leakage of serum albumin into surrounding interstitial tissues. The late time point scans also provided better contrast between inflammatory muscles and contralateral normal muscle.

Malignant tumors often show increased uptake and retention of high molecular weight non-targeted drugs and pro-drugs, which is known as enhanced permeability and retention (EPR) effect. Moreover, angiogenesis and vasculature vary in different tumor types. Thus, the ability to non-invasively evaluate tumor vasculature and permeability would be very helpful for patient pre-selection and therapy response monitoring. With $^{64}$Cu-NEB PET, it was found that UM-22B tumors are very permeable. It was noticed that TAC over the heart region showed a downslope and that over tumor region showed a plateau. The difference between these two slopes was thus used to quantify tumor vascular permeability.

Evans blue has been used clinically to evaluate the blood volume. The clinical practice has been discontinued due to the toxicity of vital dye, especially potential pulmonary embolism after intravenous injection. The mechanism of this toxicity is due to an Evans blue dose related induction of platelet aggregation, which begins with the threshold concentration of about 100 μM. For in vive PET imaging, only trace amount of $^{18}$F-AlF-NEB (~3 μg/mL or 3.6 μM) was used, which would not elicit toxicity. Even with multiple injections, the dose is expected to be safe. A dosimetry study was also performed based on the PET imaging data. For the sensitive organs such as red bone marrow, the absorbed dose is 0.23 mSv for $^{18}$F-AlF-NEB and 6.14 mSv for $^{64}$Cu-NEB if 185 MBq of radioactivity was injected into each subject. This dose allows multiple PET scans without exceeding recommended annual dose limit for diagnostic purpose.

The tracers of the invention could be used to visualize the distribution and local accumulation of serum albumin non-invasively by PET. ECG-gated $^{18}$F-AlF-NEB PET could be used to evaluate the loss of cardiac function in mice with myocardial infarction. The vascular leakage induced by acute inflammation and increased permeability in malignant tumors could also be visualized and quantified with this strategy.

Figure 1A:
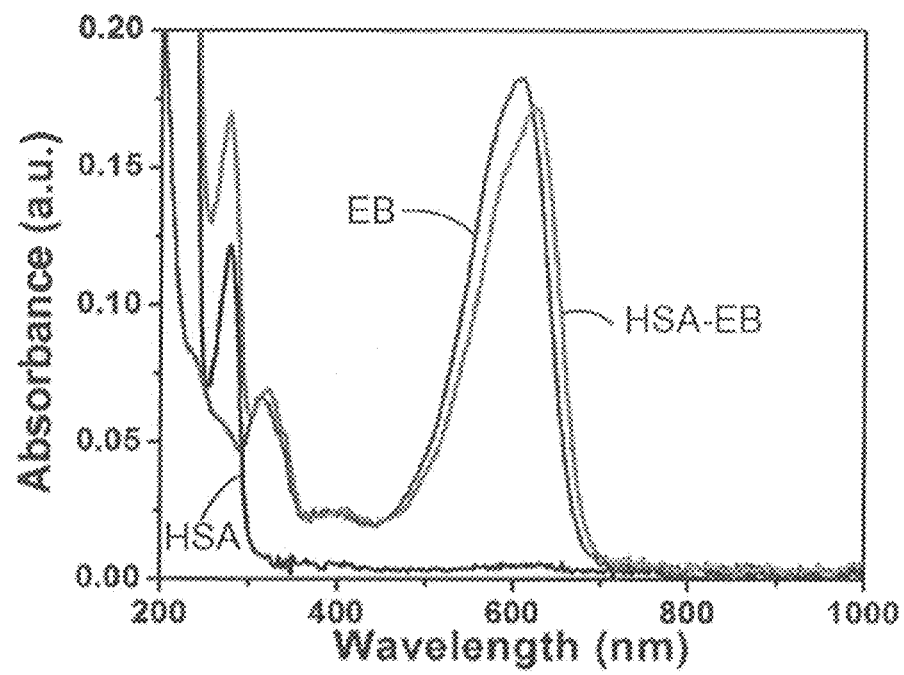
Figure 1B:
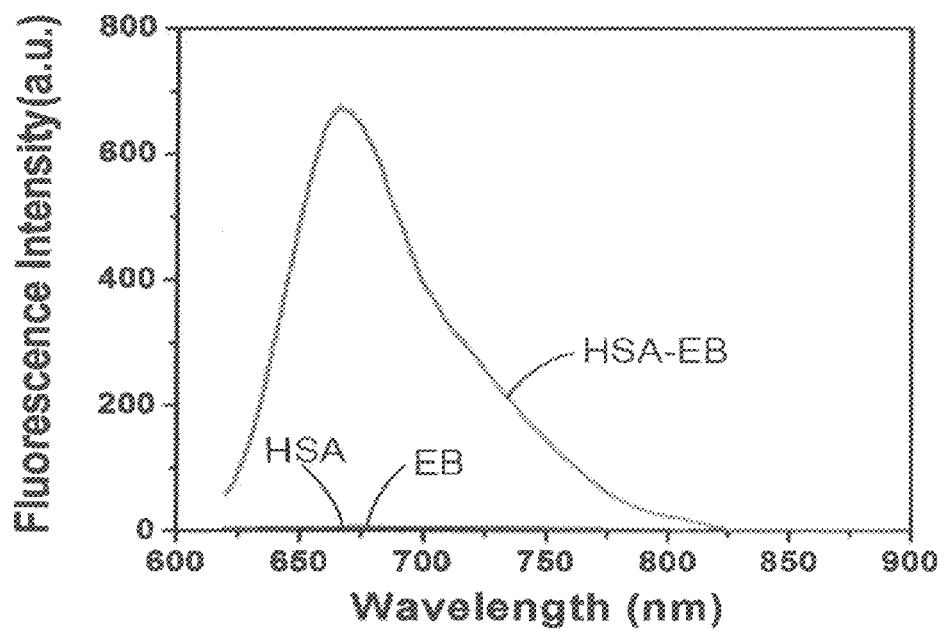

The invention further provides a lymphatic imaging agent by mixing EB with the PET tracer $^{18}$F-AlF-NEB. EB has been extensively used as a visible dye. In fact, the quantum yield of EB itself is rather low. However, like some other dye molecules, when EB forms a complex with albumin, the fluorescence emission of the complex increases dramatically (FIGS. 1A and 1B). It is widely accepted that albumin binding sterically and electronically stabilizes the fluorophore's ground state electronic distribution and increases the quantum yield. In fact, the fluorescence signal is more sensitive than the visible color. This phenomenon was taken advantage of by performing fluorescence imaging after local injection of $^{18}$F-AlF-NEB/EB, which quickly forms a complex with albumin within the interstitial fluid. The radioactive signal reflects the behavior of endogenous albumin, avoiding the usage of colloids, nanoparticles, and polymers. Thus, mixing $^{18}$F-AlF-NEB with the EB dye allows PET, visual, and fluorescence tri-modality imaging. Local lymph nodes (LNs) and the lymphatic vessels between LNs can be clearly visualized by the blue color of the dye as well as optical imaging. Furthermore, the sentinel lymph nodes can be detected by PET scans.

This imaging probe embodiment of the invention was first applied to a turpentine oil-induced hind limb inflammation model. With inflammatory stimulation, local lymph nodes undergo a series of changes in order to clear debris and provide a site for activated immune cells. This process is often coupled with an increase in size and enhanced lymphatic drainage. Turpentine oil induced tissue inflammatory responses peak at day 4. Therefore, $^{18}$F-AlF-NEB PET imaging was first performed in hind limb inflammation model on day 5 after turpentine oil injection. The popliteal and sciatic LNs on both sides can be clearly visualized from 0.5 to 3 h after tracer injection with inflamed LNs accumulating a higher amount of tracer (FIGS. 2A-2E). The imaging results corroborate with the size and flow changes during local inflammatory responses. The feasibility of imaging tumor draining LNs in an orthotopic breast tumor model was next explored. After intratumoral injection, SLNs were successfully detected by $^{18}$F-AlF-NEB PET with excellent image quality (FIG. 3).

The detection of SLNs is important in clinical cancer classification and treatment. Currently, pre-surgical diagnosis of SLNs is often based on the morphological changes observed by MR or CT scans. However, it is very challenging for MRI or CT to visualize SLNs when they are very small or have signal intensities comparable with surrounding healthy soft tissues. Based on the imaging results acquired in three different animal models, it is believed that co-injection of $^{18}$F-AlF-NEB and EB can be applied clinically for SLN detection. After local administration, PET imaging can be performed first to identify the distribution and location of SLNs around the tumor. The surgeon can then rely on visible blue color and fluorescence imaging during surgery for SLN biopsy and removal. A hand-held detector can also be used for SLN detection.

The trimodality imaging in accordance with the invention provides an excellent, non-invasive pre-surgical visualization of SLNs as well as intra-surgical guidance. The multimodal PET imaging tracer that has been developed has a great potential for clinical application due to its biosafety, excellent quality of imaging, easy preparation, and cost-effectiveness.

Co-injection of $^{18}$F-AlF-NEB and EB provides an easy method of in vive labeling of endogenous albumin in the interstitial fluid thereby enabling PET, optical fluorescence and visual trimodality imaging for highly sensitive detection of LNs and lymphatic vessels. The excellent imaging quality, easy preparation, multimodal applicability, and biosafety of this approach warrant its clinical application to map SLNs and provide intraoperative guidance.

The invention further provides a blood volume imaging agent and its use in differentiating hemangioma from other focal hepatic lesions. In a preferred embodiment, the imaging agent is $^{68}$Ga-NEB. This first-in-human study was based on a successful in vivo albumin labeling strategy with a compound in accordance with an embodiment of the invention, which forms a complex with serum albumin after intravenous injection. The labeling is very efficient without compromising the physiological behavior of the protein, thus the emitted radioactive signal reflects accurately the in vivo behavior of albumin. It also avoids unnecessary cross-contamination from blood products as is the case with labeling of RBCs for blood pool imaging. For imaging purpose, only trace amount of the compound was administered so the possible toxicity of the vital dye and potential pulmonary embolism after intravenous injection is totally avoided.

All healthy volunteers and patients reported no discomfort or adverse clinical events, no elicited toxicity, and no allergies. Dosimetry study confirmed the safety with acceptable absorbed doses by critical organs even with multiple injections for one patient. With an injected dose of 3-4 mCi (121-148 MBq), a patient would be exposed to a radiation dose of 2.65 mSv, which is much lower than the dose limit as set by the by the Food and Drug Administration (FDA).

After intravenous injection, majority of the radioactivity was retained in blood circulation due to the stable complexation of $^{68}$Ga-NEB with serum albumin. Within a few minutes after tracer injection, it reached an equilibrium reflected by the constant high SUV value in the blood. A slow but steady clearance of the radioactivity from the blood was observed. This was mainly caused by the turnover of albumin from blood circulation to the interstitial space and slight dissociation of $^{68}$Ga-NEB from albumin. The heart to liver ratios at different time points are very close to that of in vitro labeled RBCs and is significantly higher than that of in vivo labeled RBC, which confirmed the role of $^{68}$Ga-NEB as a blood pool PET imaging agent.

There are several major applications for a blood pool imaging agent including evaluation of the cardiac function, detection of vascular anomalies, and localization of neoplasms. Hepatic hemangioma is a vascular anomaly, characterized with multiple vascular channels with a single layer of benign endothelial cells. Consequently, high level of local accumulation of $^{68}$Ga-NEB was observed, making tumors highly visible against the surrounding normal hepatic tissues. Meanwhile, lesions of HCC, hepatic cyst and hepatic metastases of neuroendocrine tumors showed "negative" contrast because of the relatively low accumulation of $^{68}$Ga-NEB. The high specificity of $^{68}$Ga-NEB PET would play a very important role in differentiating hemangioma from other focal hepatic lesions.

The accurate diagnosis of hemangioma with $^{68}$Ga-NEB PET can avoid unnecessary over-treatment and biopsy, which has the risk of hemorrhage. In combination with $^{18}$F-FDG PET, $^{68}$Ga-NEB PET/CT can be of great value for differential diagnosis of cysts, hemangioma and other benign hepatic lesions from malignancy, especially in patients with history of malignancy. It is also predictable that $^{68}$Ga-NEB PET will be helpful in diagnosing hemangioma occurring in other organs.

The invention also provides an imaging composition comprising a compound of formula (I) and a pharmaceutically acceptable carrier.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described imaging compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the compound and one which has no detrimental side effects or toxicity under the conditions of use.

The choice of carrier will be determined in part by the compound, as well as by the particular method used to administer the composition. Accordingly, there is a wide variety of suitable formulations of the imaging composition of the present invention. In a preferred embodiment, the imaging composition is administered parenterally. The following formulations for parenteral administration are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the compound in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

The following examples further illustrate the invention but, of course, should not be construed as in any way limiting its scope.

General Materials and Instrumentation

The monosodium salt of 1-amino-8-naphthol-2, 4-disulfonic acid was purchased from TCI America (Portland, Oreg.) and all other chemicals were from Sigma-Aldrich (St. Louis, Mo.). Mass spectra (MS) were obtained on a Waters Acquity UPLC system coupled with Waters QT of Premier MS (LC-MS). Semi-preparative reversed-phase HPLC was performed on a Waters 600 gradient system with a Waters 996 Photodiode Array (PDA) detector using a Waters Nova-Pak HR $C_{18}$ column (6 μm, 300×7.8 mm). Analytical reversed-phase HPLC was performed on a Perkin-Elmer Series 200 LC gradient system with a Waters 2784 Dual Absorbance UV detector plus a Bioscan radioisotope detector using a Waters Symmetry column (5 μm, 150×3.9 mm). The flow rate was 6 mL/min for the semi-preparative column and 1 mL/min for the analytical column running the same linear gradient starting from 5% A (0.1% TFA in acetonitrile) and 95% B (0.1% TFA in water) for 5 min and increasing A to 65% at 35 min. Varian BOND ELUT $C_{18}$ column (100 mg) was used for solid-phase extraction of the labeled product. $^{18}$F-fluoride and $^{64}$CuCl$_2$ were obtained from the NIH cyclotron facility.

Animal Models

All animal studies were conducted in accordance with the principles and procedures outlined in the Guide for the Care and Use of Laboratory Animals and were approved by the Institutional Animal Care and Use Committee of the Clinical Center, NIH. The UM-22B human head and neck carcinoma cancer cell line was grown in DMEM medium supplemented with 10% fetal bovine serum (FBS), 100 IU/mL penicillin, and 100 μg/mL streptomycin (Invitrogen), and in a humidified atmosphere containing 5% $CO_2$ at 37° C. The tumor model was developed in 5 to 6 week old female athymic nude mice (Harlan Laboratories) by injection of 5×10$^6$ cells into their right shoulders. The mice underwent small-animal PET studies when the tumor volume reached 100-300 mm$^3$ (2-3 weeks after inoculation).

Myocardial infarction (MI) model was prepared in male Balb/c mice aged from 8 to 10 weeks. MI was induced by ligation of the left anterior descending coronary artery 1-3 mm from the tip of the left auricle with a 7-0 polypropylene suture. The occlusion and reperfusion were confirmed by ST-segment elevation on an electrocardiogram (ECG) monitor (EC-60 model; Silogic) after surgery. For mice in the control group, the surgery was performed but without ligation of the left coronary artery.

The acute inflammation model was prepared by intramuscular injection of turpentine. Up to 30 μL turpentine was injected in the caudal thigh muscles of left hind limb. The PET imaging was performed 24 h after turpentine injection.

Small-Animal PET Imaging and Analysis

PET scans and image analysis were performed using an Inveon small animal PET scanner (Siemens Medical Solutions). About 3.7 MBq of $^{18}$F-AlF-NEB or $^{18}$F-FB-Albumin or 7.4 MBq of $^{64}$Cu-NEB was administered via tail vein injection under isoflurane anesthesia. For normal mice, 60-min dynamic PET scans were acquired. For tumor mice, 60-min dynamic PET scans were acquired, followed by a series of late time point scans at 2, 4, and 24 h ($^{64}$Cu only) after tracer injection. With acute inflammation model, 5-min static PET images were acquired at 30 min, 1 h and 2 h postinjection (n=3-5 per group). The images were reconstructed using a two-dimensional ordered-subset expectation maximum (2D OSEM) algorithm, and no correction was applied for attenuation or scatter. For each scan, regions of interest (ROIs) were drawn using vendor software (ASI Pro 5.2.4.0) on decay-corrected whole-body coronal images. The radioactivity concentrations (accumulation) within the heart, muscle, liver, and kidneys were obtained from mean pixel values within the multiple ROI volume and then converted to MBq per milliliter. These values were then divided by the administered activity to obtain (assuming a tissue density of 1 g/ml) an image-ROI-derived percent injected dose per gram (% ID/g).

For ECG gated PET studies, mice were imaged in a prone position within the PET scanner, and were kept at 37° C. using a heating pad with continuous rectal measurement of body temperature. ECG electrodes were placed on the forepaws and the left hindpaw. Respiration was measured using a small pressure detector lying under the thorax of the mice. The cardiac excitation and respiration were recorded with a Biovet system (Spin Systems Pty Ltd.) throughout the scan. A list-mode PET scan of 30 min was acquired at 15 min after intravenous injection of around 3.7 MBq of $^{18}$F-NEB (both control and MI models), respectively. The cardiac cycle from the $^{18}$F-NEB list-mode acquisitions was separated into eight equal intervals using the Siemens Inveon Acquisition Workplace and reconstructed using OSEM 3D with four iterations and MAP 3D with 32 iterations. The measurements of LV function from the PET data sets were calculated and quantified using the Inveon Research Workplace (IRW, Siemens Preclinical Solutions). A 55% intensity threshold was used for the quantitation of LVEF.

Preclinical PET Imaging and Dosimetry Evaluation.

For dynamic PET scans, four BALB/C mice were injected intravenously with 1.85 MBq (50 μCi) of $^{68}$Ga-NEB under isoflurane anesthesia. A 60 min list mode acquisition was performed with an Inveon PET scanner (Siemens Preclinical Solutions, PA, USA). Image reconstruction was done by the 2-dimensional ordered subsets expectation maximum (OSEM) algorithm without attenuation or scatter correction. Regions of interest (ROIs) over major organs were drawn on decay-corrected whole-body coronal images for each PET scan, using vendor software (ASI Pro 5.2.4.0). The radioactivity concentration (accumulation) within a tumor or an organ was obtained from mean pixel values within the multiple ROI volume, after conversion of the values to MBq/mL/min by using a conversion factor. The conversion to MBq/g/min assumed a tissue density of 1 g/mL. Imaging ROI-derived % ID/g was calculated by dividing the ROIs by the administered activity.

For ex vivo biodistribution and dosimetry evaluation, each BALB/C mouse was injected with 1.85 MBq of $^{68}$Ga-NEB. At different time points after tracer injection (5 min, 30 min, 1 h, 3 h and 6 h, n=5/time point), the mice were sacrificed for tissue and organ collection, including blood, muscle, bone, liver, kidneys, spleen, pancreas, stomach, intestine, heart and lung. The samples were wet weighed, and measured for radioactivity in a γ-counter (Wallac 1470-002, Perkin-Elmer). The results were presented as percentage injected dose per gram of tissue (% ID/g). For each mouse, the radioactivity of the tissue samples was calibrated against a known aliquot of the injected tracer and normalized to a mean body mass of each group. Values were expressed as mean±SD (n=5/group). Determination of organ doses for a reference human male was made using the OLINDA/EXM program (Vanderbilt University, Nashville, Tenn.).

Volunteers and Patients Recruiting.

This clinical study was approved by the Institute Review Board of Peking Union Medical College Hospital, Chinese Academy of Medical Sciences and Peking Union Medical College. Three healthy volunteers (2 males and 1 female) were enrolled with written informed consent to validate the safety of $^{68}$Ga-NEB. No fasting, hydration or other specific preparation was requested on the day of imaging. Any unusual or adverse clinical symptoms were recorded on the day of imaging and during the 2-week follow-up period.

All patients were 18 years old or above, capable of understanding the study and signed a written informed consent. A total of 11 patients with hepatic space-occupying lesions were recruited. The final diagnosis was based on pathological result of surgical removal or biopsy. Among the recruited patients, 4 patients were diagnosed with hemangioma, 5 with primary hepatic carcinoma, 1 with neuroendocrine tumor liver metastases and 1 with hepatic cyst.

PET Imaging Procedures.

All three healthy volunteers underwent whole-body PET acquisitions (Biograph mCT PET/CT system, Siemens) at multiple time points after tracer injection. After the whole-body low-dose CT scan (140 kV, 35 mA, pitch 1:1, layer 5 mm, layer spacing 3 mm, matrix 512×512, FOV 70 cm), 111-148 MBq (3-4 mCi) of $^{68}$Ga-NEB was injected intravenously. The whole body (from the top of skull to the middle of femur) of each volunteer was covered by 7 bed positions. The acquisition duration was 40 sec/bed position for the 5 min, 10 min and 15 min time points, 2 min/bed position for the 30 min, 45 min, 60 min, 75 min and 90 min time points.

All patients underwent whole-body PET/CT acquisitions at 30-45 min after intravenous injection of 111-148 MBq (3-4 mCi) of $^{68}$Ga-NEB with each bed position lasting for 2 min. The acquisition field covered from the top of skull to the middle of femur with 6 or 7 bed positions, depending on the height of the patient. A standard $^{18}$F-FDG PET/CT was acquired with the same patients within one week.

Image and Data Analysis.

A Siemens MMWP workstation was used for post-processing. Visual analysis was used to determine the general biodistribution and the temporal and inter-subject stability. The volume of interest (VOI) of 12 normal organs/tissues and concerned lesions were drawn on the serial images. The radioactivity concentration and standardized uptake value (SUV) in the VOIs were obtained through the software. Organ dosimetry was calculated by using organ-level internal dose assessment software. All quantitative data were expressed as mean±standard deviation.

Hematoxylin and Eosin Staining

Tissues were collected and fixed in Z-fix (buffered zinc formalin fixatives, Anatech, Mich.) for at least 24 h, then embedded in paraffin for sectioning. The slices (10 μm) were stained with hematoxylin and eosin by standard techniques. The stained tissue sections were observed with a BX41 bright field microscopy (Olympus).

Statistical Analysis

Quantitative data were expressed as mean±SD. Means were compared using Student's t test provided by Excel (Microsoft) or GraphPad Prism (GraphPad Software, Inc.). P value of <0.05 was considered statistically significant.

Example 1

This example demonstrates a synthesis of the compound:

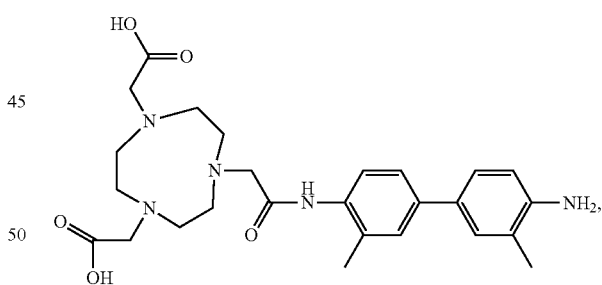

in accordance with an embodiment of the invention.

To a 4 mL glass vial containing 20.0 mg of o-tolidine (94 μmol) and 20.0 mg of 1, 4, 7-triazacyclononane-N,N',N"-triacetic acid-3HCl ("NOTA") (48 μmol) in 1 mL of DMSO was added 3.6 μL of diethyl cyanophosphonate (24 μmol) and 25 μL of diisopropylethylamine (DIPEA). The mixture was stirred at room temperature for 40 min and another 3.6 μL of diethyl cyanophosphonate was added and stirred at room temperature overnight. The mixture was then purified with semi-preparative HPLC. The peak containing the desired product was collected ($R_t$=10.0 min) and the solution was frozen over dry ice and lyophilized overnight to give 12.2 mg pure product in 26.4% yield. LC-MS ($C_2H_{35}N_5O_5$): [MH]$^+$=498.2467 (m/z), calc: 497.2638.

Example 2

This example demonstrates a synthesis of the compound:

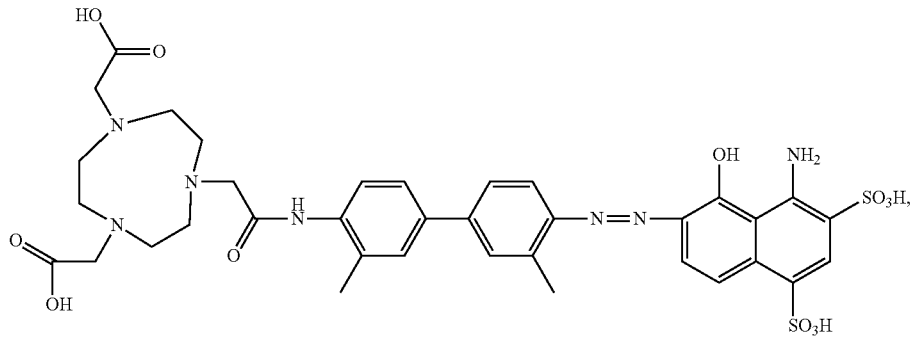 [SMILES: Cc1cc(-c2ccc(NC(=O)CN3CCN(CC(=O)O)CCN(CC(=O)O)CC3)c(C)c2)ccc1N=Nc1ccc2c(S(=O)(=O)O)cc(S(=O)(=O)O)c(N)c2c1O]

in accordance with an embodiment of the invention.

To a 20 mL glass vial containing 2.5 mg of NOTA-tolidine (5.0 μmol) in 0.3 mL of water was added 18 μmol of HCl in 0.1 mL of water. The mixture was cooled in ice bath and 0.5 mg of sodium nitrite (7.2 μmol) in 0.1 mL of water was added to the vial. The mixture was stirred in ice bath for 20 min and the yellow diazonium salt solution was added dropwise to another vial in ice bath containing 4.0 mg of 1-amino-8-naphthol-2,4-disulfonic acid (10.0 mol) and 2.4 mg of sodium bicarbonate (28.5 μmol) in 0.2 mL of water. The mixture was stirred in ice bath for 2 h and purified with semi-preparative HPLC. The product (denoted as NEB) was collected ($R_t$=19.0 min) and lyophilized overnight to give 1.4 mg pure product in 46.6% yield. LC-MS ($C_{36}H_{41}N_7O_{12}S_2$): [M-H]$^-$=826.2415 (m/z), calc: 827.2255.

Example 3

This example demonstrates a synthesis of the compound:

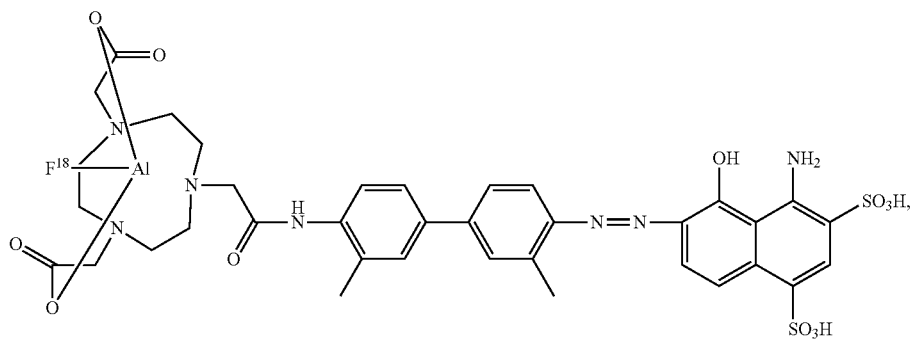

in accordance with an embodiment of the invention.

To a 1 mL plastic tube containing 3 μL of 2 mM aluminum chloride in 0.5 M pH 4.0 sodium acetate buffer and 6 μL, of 3 mM NEB in 0.5 M pH 4.0 sodium acetate buffer was added 0.13 mL acetonitrile and 0.05 mL of aqueous $^{18}$F-fluoride (0.3-0.9 GBq). The mixture was vortexed and heated in a 105° C. heating block for 10 min. The vial was cooled, and the solution was diluted with 10 mL of water and trapped on a Varian Bond Elut $C_{18}$ column (100 mg). The radioactivity trapped on the $C_{18}$ column was eluted with 0.3 mL of 80% ethanol/water containing 1 mM HCl. The ethanol solution was evaporated with argon flow, and the final product was dissolved in PBS and analyzed by HPLC.

Example 4

This example demonstrates a synthesis of the compound:

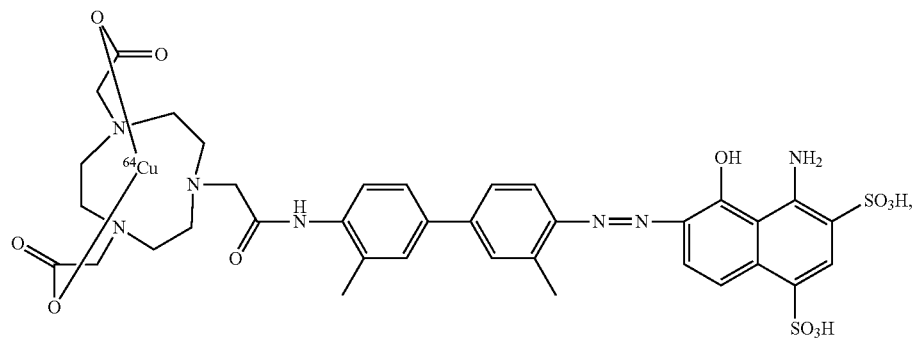

in accordance with an embodiment of the invention.

To a 1 mL plastic tube containing 11.0 μg of NEB in 100 μL of 0.4 M pH 5.5 sodium acetate buffer was added 5 μL of aqueous $^{64}$Cu—CuCl$_2$ solution (262.7 MBq). The mixture was vortexed and heated on an 80° C. heating block for 10 min. The tube was cooled, and the radioactive solution transferred to a 10 mL syringe containing 10 mL of water. This solution was passed through a Varian Bond Elut Cis cartridge (100 mg) and the desired product was trapped on the cartridge. The radioactivity trapped on the C$_{18}$ column was eluted with 0.45 mL of 80% ethanol/water with 1 mM HCl to give 185 MBq of the desired product in 70% radiochemical yield. The ethanol solution was evaporated with argon flow, and the final product was dissolved in PBS and analyzed by HPLC. The radiochemical purity was >95%.

Example 5

This example demonstrates a synthesis of the compound:

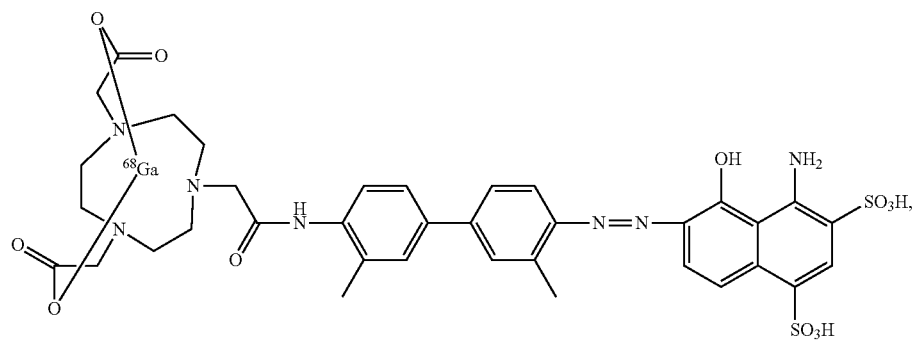

in accordance with an embodiment of the invention.

The NOTA conjugate of truncated form of Evans blue (NEB) was synthesized according to a method described in our previous publication (Niu, G. et al., *J. Nucl. Med.*, 2014, 55(7): 1150-1156). $^{68}$Ga was eluted from a $^{68}$Ge/$^{68}$Ga generator (ITG, Berlin, Germany) using 0.05 M HCl and mixed with 1.25 M NaOAc buffer to adjust the pH value to 4.0. The mixture was then directly transferred to a 1 mL plastic tube containing 30 μg of NEB. After shaking, the mixture was incubated in a heating block at 100° C. for 10 min. The reaction mixture was then cooled down, dissolved in sterile phosphate-buffered saline (PBS) and passed through 0.22 μm aseptic filtration membrane. The quality control was performed with analytical HPLC and thin layer chromatography (BIOSCAN, USA). CH$_3$OH:NH$_4$OAc (v/v 1:1) was used as the developing solution for TLC. The radiochemical purity was greater than 95%.

Example 6

This example demonstrates a preparation of $^{18}$F-fluorobenzyl albumin.

N-succinimidyl 4-$^{18}$F-fluorobenzoate ($^{18}$F-SFB) was prepared with an Eckert & Ziegler synthesizer according to a published procedure (Chen, X. et al., *Eur. J. Nucl. Med. Mol. Imaging*, 2004, 31: 1081-1089). The HPLC purified $^{18}$F-SFB was trapped on a Waters C-18 cartridge and eluted with 1 mL methylene chloride into a 1 mL plastic tube. For a typical run, after evaporation of solvent, the radioactivity (148 MBq) was re-dissolved in 5 μL of acetonitrile and 0.5 mg of mouse serum albumin (MSA) in 100 μL, of pH 8.5 borate buffer was added to the tube and reacted at 37° C. for 10 min. The reaction mixture was purified on a PD-10 size exclusion column to give 92.5 MBq of product in 62.5% radiochemical (non-decay-corrected) yield.

Example 7

This example demonstrates in vivo PET imaging of normal mice, in accordance with an embodiment of the invention.

The in vivo pharmacokinetics of $^{18}$F-AlF-NEB was evaluated with dynamic PET in healthy Balb/C mice. As expected, most of the radioactivity was retained in the circulation system during the first 60 min postinjection (p.i.). Ventricles of the heart and major arteries were clearly visualized on PET images. The locations of liver, kidneys, and spleen were also identified due to the abundant blood supply of these organs (FIG. 4). Based on the time-activity curves generated by PET images, whole blood radioactivity was only decreased by 10% from 10 to 60 min p.i. Organs with a large blood volume such as liver, spleen and kidneys showed higher uptakes than the skeletal muscle but were considerably less than the blood cavities within the heart and main branches of the blood vessels. Counts in the heart VOI rapidly peaked at 1 min p.i., then declined gradually but remained higher than those in the liver and kidneys. The radioactivity in the bladder increased continuously with time (FIG. 5A). HPLC analysis of urine sample found that the radioactivity came from both intact $^{18}$F-AlF-NEB and its metabolites. In blood samples, the majority of the radioactivity was from the intact $^{18}$F-AlF-NEB.

The in vivo labeling by $^{18}$F-AlF-NEB was also compared with in vitro labeled $^{18}$F-FB-MSA. The PET results showed very similar distribution pattern between the two probes. The blood and liver time-activity curves from $^{18}$F-FB-MSA showed slightly less but non-significant (p>0.05) decline rate than those of $^{18}$F-AlF-NEB. The bladder showed almost no uptake of $^{18}$F-FB-MSA within the first 20 min but increased dramatically afterwards. At 60 min p.i. of $^{18}$F-FB-MSA, the radioactivity in the bladder was much higher than that in the blood (FIGS. 5A and 5B).

After PET imaging, the animals were sacrificed and major tissues and organs were collected. The radioactivity was measured and the results were presented in Table 1. With both $^{18}$F-AlF-NEB and $^{18}$F-FB-MSA, the blood had the highest counts. The radioactivity levels in the liver, kidneys and spleen for $^{18}$F-FB-MSA (in vitro labeling) were significantly higher than those for $^{18}$F-AlF-NEB (in vive labeling).

TABLE 1

| Tracer | Blood | Muscle | Liver | Kidney | Spleen | Pancreas | Intestine |
|---|---|---|---|---|---|---|---|
| $^{18}$F-AlF-NEB | 26.35 ± 1.52 | 1.80 ± 0.48 | 5.05 ± 0.13 | 6.80 ± 1.16 | 3.75 ± 0.48 | 2.17 ± 1.38 | 4.42 ± 3.00 |
| $^{18}$F-FB-MSA | 34.71 ± 3.29 | 0.80 ± 0.09 | 7.42 ± 053 | 12.01 ± 05.59 | 8.52 ± 1.71 | 2.09 ± 0.15 | 3.10 ± 0.28 |

Example 8

This example demonstrates ECG-gated PET imaging and its use in measuring left ventricular volume over the cardiac cycle, in accordance with an embodiment of the invention.

One of the major applications of blood pool imaging is to evaluate cardiac function. The probe was first tested in normal Sprague-Dawley rats. On the representative transaxial and coronal images of $^{18}$F-AlF-NEB, the fine septal borders between the left and right ventricle were clearly identified. The major arteries and vena cava were also visualized. After dividing each cardiac cycle into eight fragments, the end-systole and end-diastole can be easily distinguished.

A mouse myocardial infarction (MI) model was also developed and performed ECG gated PET with the similar procedure. The cardiac cycle with eight fragmentations is presented in FIG. 6. Although limited by the much smaller size of mouse heart and spatial resolution of PET, the ventricles can be clearly distinguished. The end-systole volume of MI mice was significantly higher than that in the control mice. Based on PET images, left ventricular (LV) volume over the cardiac cycle was generated and shown in FIG. 7A. The MI mice showed much lower LVEF than the control mice (79.54±2.95% vs. 60.24±6.88%, P<0.01) (FIG. 7B). Ultrasound was also performed with the same two groups of mice. The LVEF results determined by US were consistent with those from PET imaging.

Example 9

This example demonstrates PET imaging of vascular leakage, in accordance with an embodiment of the invention.

An acute skeletomuscular inflammation model was developed by local intramuscular injection of turpentine and $^{18}$F-AlF-NEB PET was performed to evaluate the images for vascular leakage. The inflammation induced by local intramuscular injection of turpentine was indicated by neutrophil infiltration on HE staining (FIG. 8). As shown in FIG. 9, high level of radioactivity accumulation was observed within inflamed muscles at 1 and 2.5 h after $^{18}$F-AlF-NEB administration. Indicated by the time activity curves (TACs) of 60-min dynamic imaging, the tracer uptake in the inflammatory muscles increased gradually along with time while no apparent changes were observed in TACs of the collateral muscles (FIG. 10). Quantitative analysis of PET images indicated an uptake of 5.94±0.69% ID/g at 1 h after $^{18}$F-AlF-NEB injection and 7.50±0.69% ID/g at 2.5 h p.i. (FIG. 11).

Example 10

This example demonstrates PET imaging of tumor vasculature, in accordance with an embodiment of the invention.

Malignant tumors are characterized by torturous blood vessels and high vascular permeability. Besides, the anti-angiogenesis and "normalization" of tumor vasculature have been intensively investigated. Unlike radiolabeled RBCs, albumin can be used to study vascular permeability in tumors. NEB was labeled with $^{64}$Cu, a positron emitter with longer half-life ($t_{1/1}$=12.6 h) than $^{18}$F ($t_{1/2}$=109.8 min). A UM-22B xenograft model was developed and performed 60-min dynamic scan and then static scans at late time points up to 24 h. The in vivo distribution of $^{64}$Cu-NEB was very similar to that of $^{18}$F-AlF-NEB with most of radioactivity retained in the circulation system (FIG. 4A). Even at 4 h after tracer injection, radioactivity within heart region and major vessels was still dominant. The tumor uptake was 5.73±1.11% ID/g at 1 h p.i. and increased to 8.03±0.77% ID/g at 2 h p.i. At 24 h after tracer injection, the tumor uptake was still at a relatively high level (8.07±1.01% ID/g). The tracer uptake over the heart region was 16.09±0.51% ID/g at 1 h p.i., which dropped to 8.58±0.81% ID/g at 24 h (FIG. 5B).

Example 11

This example demonstrates PET imaging of inflamed lymph nodes, in accordance with an embodiment of the invention.

Figure 2A:
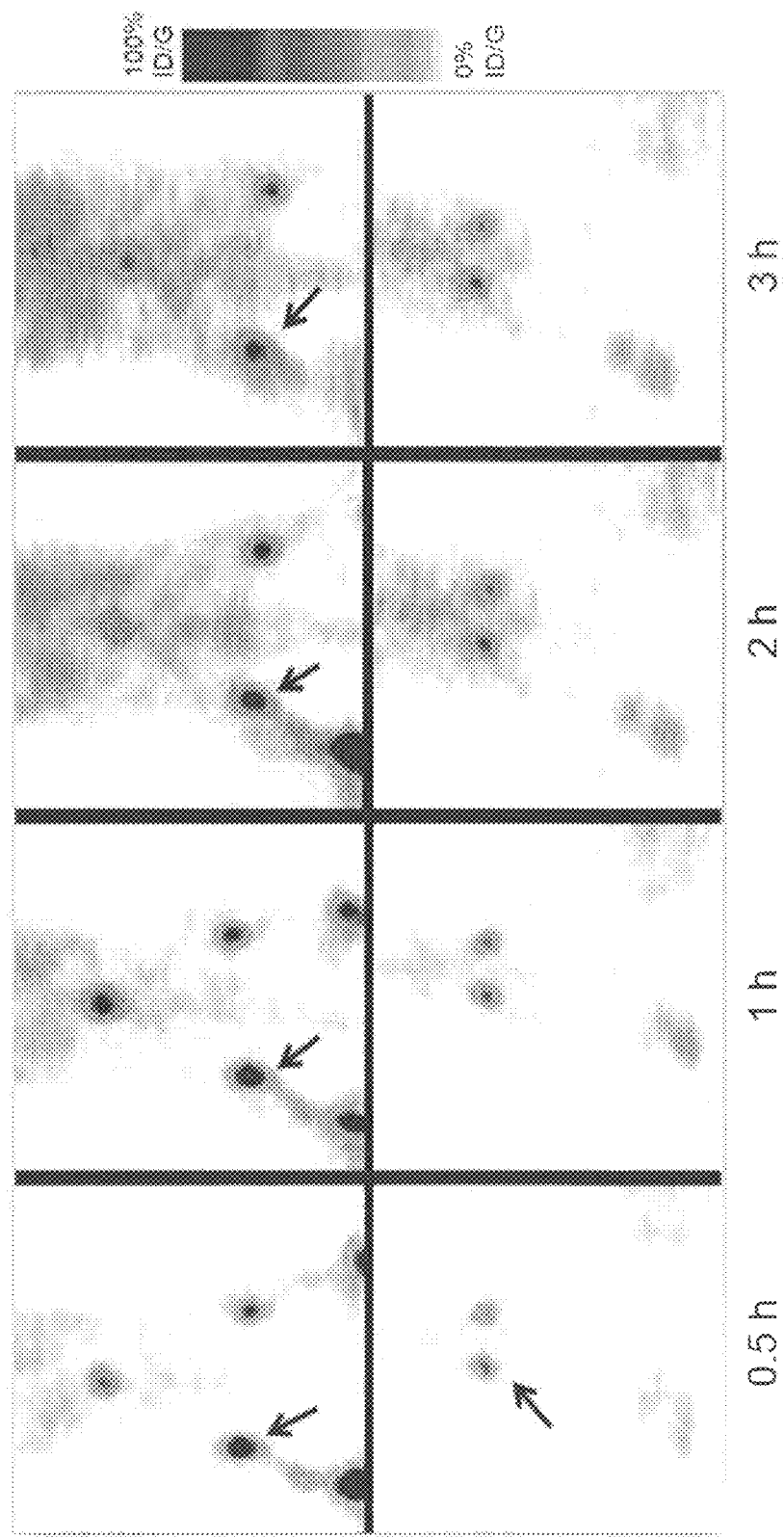
FIG. 2A shows representative reconstructed coronal PET images of inflamed popliteal (upper) and sciatic (lower) LNs in the turpentine oil-induced hind limb inflammation model. LNs were pointed out by arrows.
Figure 2B:
FIG. 2B show the $T_2$-weighted NRI of an enlarged inflamed popliteal LN, as indicated by the arrow.
Figure 2C:
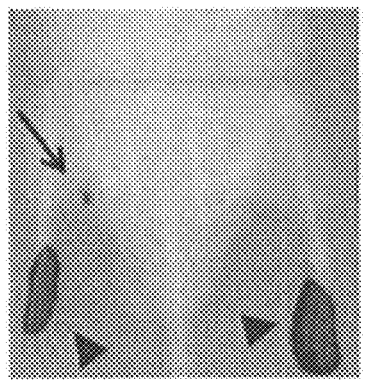
FIG. 2C shows the overlay of PET with a 2D X-ray image. The LN is indicated by an arrow and the injection sites by arrowheads.
Figure 2D:
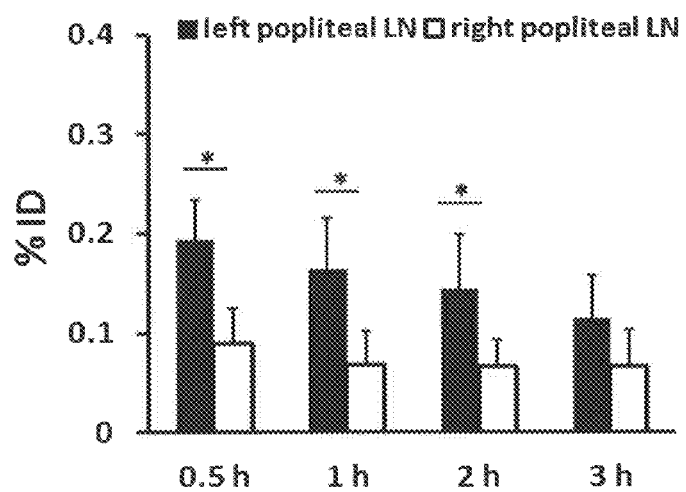
FIG. 2D shows quantitative analysis based on the PET images of FIGS. 2A-2C. There is significantly higher total tracer uptake in inflamed popliteal LNs than that of contralateral normal LNs at 0.5, 1, 2, and 3 h after tracer injection (*P<0.05)
Figure 2E:
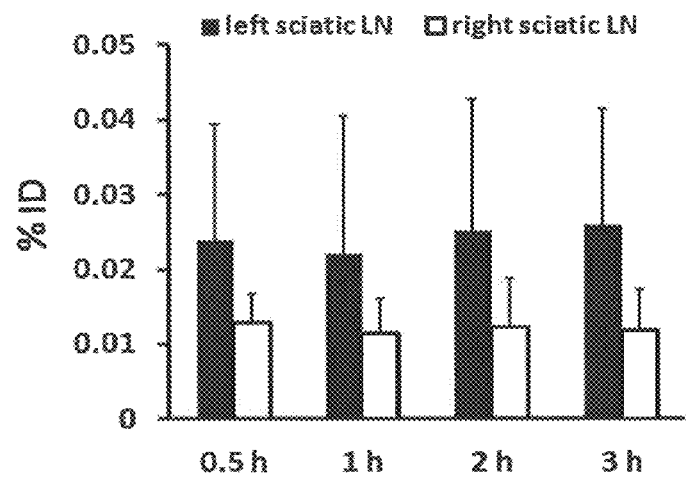
FIG. 2E shows quantitative analysis of tracer uptake in sciatic LNs. No statistical significance was found between LNs in the left and right side.

$^{18}$F-AlF-NEB PET imaging was performed on day 5 after turpentine injection. As shown in FIG. 2A, popliteal lymph nodes (LNs) on both sides were clearly seen on PET images with a high signal to background ratio at all the time points examined. Due to the inflammatory stimulation, the left popliteal LNs had an obviously higher tracer uptake than the contralateral normal LNs. The left sciatic LNs also showed slightly higher signal intensity. Corresponding $T_2$-weighted MR images confirmed swelling of the popliteal LNs (FIG. 2B) but not the sciatic LNs. Overlay of PET images with x-ray confirmed the anatomic location of the popliteal LNs (FIG. 2C). Quantification of the PET images showed uptake of $^{18}$F-AlF-NEB in the left popliteal LN was 0.195±0.039% ID, which was significantly higher than that in the right popliteal LN (0.09±0.035% ID, p<0.05) at 0.5 h p.i. The signal intensity in the left popliteal LN dropped to 0.116±0.052% ID at 3 h time point (FIG. 2D). As shown in FIG. 2E, although the left sciatic LN had somewhat higher tracer uptake than the right sciatic LN, no significant difference was found (p>0.05).

Example 12

This example demonstrates PET imaging of tumor draining lymph nodes, in accordance with an embodiment of the invention.

Thirty days after tumor inoculation, female nude mice bearing orthotopic MDA-MB-435 breast cancer tumors were scanned following intra-tumoral injection of $^{18}$F-AlF-NEB. As shown in FIG. 3A-3C, besides the tracer injection site, a satellite spot with high signal intensity was identified on PET images firm three orientations (coronal, sagittal and transaxial) of the same mouse. Using a reference map of the lymphatic system of rodent mammary fat pad, the hot spot was identified as the accessory axillary LN. In order to confirm this, one mouse was sacrificed after PET imaging and the right accessory axillary LN was removed (FIG. 3D). Ex vivo PET image showed that tumor draining-axillary LN had apparent uptake of $^{18}$F-AlF-NEB (FIG. 3E). Furthermore, another hot spot was observed in the neck area, which, according to the anatomy of murine LNs, might be a LN belonging to the cervical LN group (FIG. 3F). PET imaging of mice at day 60 after tumor inoculation was also performed; both axillary LN and cervical LN could be detected by $^{18}$F-AlF-NEB PET (FIGS. 14A and 14B). However, no tumor metastasis was observed with H&E staining of axillary LNs.

Example 13

This example demonstrates PET imaging of metastatic lymph nodes, in accordance with an embodiment of the invention.

$^{18}$F-AlF-NEB PET was also applied to image tumor metastatic LNs. Four weeks after inoculation of Fluc$^+$4T1 cells via hock injection, obvious bioluminescence signal could be seen at the popliteal fossa by bioluminescence imaging (BLI) (FIG. 15A). $T_2$-weighted MR image also showed enlarged tumor-side popliteal LNs (FIG. 15B). Immunofluorescence staining with anti-luciferase antibody confirmed the existence of tumor metastasis in the left popliteal LN (FIG. 15C). The average long-axis diameter of left LN measured by MRI was also significantly larger than that of the right one (FIG. 16).

$^{18}$F-AlF-NEB PET was performed one day after MRI. Both popliteal LNs could be visualized in 4 out of 6 mice. As seen in FIG. 17A, there were dramatically higher tracer uptake in tumor draining popliteal LNs compared with the contralateral LNs at all the time points measured. Additionally, the signal intensity of left LNs remained high after 1 h and then decreased slowly over a 3 h period. The contralateral LNs showed a similar trend but with much lower signal intensity. Autoradiography at 3 h after tracer injection displayed heterogeneity of tracer distribution inside the LN. The decreased radioactivity area observed on LN slice may be due to local tumor metastasis (FIG. 17B). Quantitative results demonstrated that the total tracer uptake of tumor metastatic LNs dropped slightly with time from 0.5 to 3 h. The values were significantly higher than those of LNs from right side (FIG. 17C). In two of the six mice, no apparent tracer uptake in the tumor-side popliteal LNs was detected. However, both the sciatic and inguinal LNs from the tumor side could be clearly seen on PET images and had much higher signal intensity than the LNs on the contralateral side (FIGS. 18A and 18B). To confirm the quantitative PET results, an ex vivo biodistribution study was carried out and the results are presented in FIG. S3. Thirty min after tracer injection, majority of radioactivity remained at the injection sites in both paws. Consistent with PET, direct tissue sampling showed significantly higher tracer accumulation in the left popliteal LNs than that in the contralateral LNs (p<0.05).

Tumor metastasis in the draining LNs was confirmed by H&E staining. As shown in FIG. 18C, healthy LNs consisted of mainly immune cells with relatively large nuclei and small amount of cytoplasm. Conversely, part of the tumor draining LNs, especially subscapular sinus area, was occupied by cells with irregular nuclei, which were tumor-metastatic foci (FIG. 18D). Foci of micrometastasis were also found inside some of the tumor draining LNs (FIGS. 18E and 18F).

Example 14

This example demonstrates multimodal imaging of lymph nodes, in accordance with an embodiment of the invention.

Since NEB showed similar albumin binding compared with EB dye, LN visual imaging was performed after co-injection of $^{18}$F-AlF-NEB and EB. Ninety min after local injection, both popliteal LN sites could be distinguished clearly by the apparent blue color, indicating the local accumulation of the dye molecules. The left sciatic LNs could also be seen but with much lower uptake of dye (FIGS. 19A and 19B). There was significant difference in weight between the popliteal LNs on the tumor side and the contralateral side but not between the sciatic LNs (popliteal LNs: 3.582±0.762 vs. 1.995±0.759 mg, p<0.05; sciatic LNs: 1.558±0.731 vs. 1.403±0.632 mg, p>0.05) (FIG. 20). The total amount of EB dye in each group of LNs was measured and the results are shown in FIG. 21. Left popliteal LNs contained 0.144±0.034 µg EB dye on average, which was significantly higher than that of the right ones (0.091±0.029 µg, p<0.05). However, there was no difference in the amount of EB between two sciatic LNs (0.030±0.008 µg vs. 0.028±0.015 µg, p>0.05). These ex vivo results were consistent with in vivo PET data.

After forming a complex with serum albumin, both NEB and EB became fluorescent. Since only trace amount of NEB was mixed with EB, the majority of the fluorescence came from EB. EB showed a strong absorbance peak at 620 nm with or without albumin. However, only with albumin, EB had a fluorescence emission peak at 680 nm (FIG. S5). With optical imaging, the migration of the injected EB/NEB in lymphatics could be clearly observed after local injection.

The fluorescence signal first reached the popliteal LN then migrated to the sciatic LN (FIG. 22). Ninety min after tracer injection, both LNs were clearly visualized by fluorescence optical imaging. Under bright light, apparent blue dye accumulation could also be seen by the naked eye (FIGS. 23A and 23B). PET and optical imaging were also performed with the same animal after injection of $^{18}$F-AlF-NEB/EB. An overlay of the two images provided high positional correlation of the LNs (FIGS. 24A and 24B).

Example 15

This example demonstrates in vivo dynamic PET imaging and biodistribution in normal mice, in accordance with an embodiment of the invention.

To investigate the pharmacokinetics of $^{68}$Ga-NEB, 1 h dynamic PET was performed in healthy BALB/C mice. After tail vein injection, most of the radioactivity from $^{68}$Ga-NEB was retained in the blood circulation, including the ventricles of the heart, major arteries and blood-enriched organs, during the entire period of observation (FIGS. 25 and 26).

In order to estimate the safe dose for clinical use, an ex vivo biodistribution study was performed in normal Balb/C mice. Absorbed doses for major organs and whole body were then extrapolated to adult human male of a body weight of 73.7 Kg using OLINDA EXM software. The mean dose ranges from 5 mice at each time point are listed in Table 2. The kidneys received the highest absorbed doses (mean absorbed dose, 0.104~0.135 mSv/MBq), resulting from abundant blood supply and tracer excretion through the renal urinary tract. The mean effective dose of $^{68}$Ga-NEB was 0.0151 to 0.0159 mSv/MBq. With an injected dose of 185 MBq (5 mCi), the patient would be exposed to an effective radiation dose of 2.94 mSv, which is much lower than the dose limit of 20 mSv for the second risk category defined by the 2007 International Commission on Radiological Protection.

TABLE 2

| Target organ | Absorbed Dose |
| --- | --- |
| Adrenals | 0.01370~0.01410 |
| Brain | 0.00868~0.01040 |
| Breasts | 0.00881~0.01000 |
| Gallbladder Wall | 0.01470~0.01490 |
| LLI Wall | 0.01040~0.01190 |
| Small Intestine | 0.01140~0.01280 |
| Stomach Wall | 0.01170~0.01270 |
| ULI Wall | 0.01150~0.01280 |
| Heart Wall | 0.03290~0.04530 |
| Kidneys | 0.10400~0.13500 |

TABLE 2-continued

| Target organ | Absorbed Dose |
| --- | --- |
| Liver | 0.04440~0.05750 |
| Lungs | 0.01970~0.02360 |
| Muscle | 0.00946~0.01100 |
| Ovaries | 0.01080~0.01220 |
| Pancreas | 0.06250~0.08210 |
| Red Marrow | 0.00882~0.00973 |
| Osteogenic Cells | 0.01330~0.01530 |
| Skin | 0.00804~0.00925 |
| Spleen | 0.02630~0.03170 |
| Testes | 0.00896~0.01030 |
| Thymus | 0.01010~0.01120 |
| Thyroid | 0.00936~0.01070 |
| Urinary Bladder Wall | 0.01020~0.01170 |
| Uterus | 0.01080~0.01230 |
| Total Body | 0.01460~0.01460 |
| Effective Dose Equivalent | 0.02510~0.02970 |
| Effective Dose | 0.01510~0.01590 |

Example 16

This example demonstrates dosimetry of an imaging compound in healthy volunteers, in accordance with an embodiment of the invention.

With a mean injected dose of 3.77±0.28 mCi, no adverse symptoms were noticed and/or reported during the entire procedure and 2 weeks follow-up, demonstrating the safety of the tracer. A representative PET image acquired at 30 min after intravenous administration of $^{68}$Ga-NEB is presented in FIGS. 27A and 27B. Cardiac ventricles, major arteries and veins showed the highest signal density. Vessel branches in and out of major organs and limbs can also be clearly identified. The liver, spleen and kidneys are also visible with relatively lower activity whereas the bladder showed high activity.

From 5 to 90 min, no dramatic distribution change was observed, confirming the in vivo stability and long blood pool retention of $^{68}$Ga-NEB (FIG. 28). Increased bladder accumulation was observed over time. The average standardized uptake values in the major organs and tissues are listed in Table 3. Although the blood vessels in the brain showed high radioactivity, the normal brain tissue had negligible accumulation of $^{68}$Ga-NEB, indicating that the tracer does not cross the blood-brain barrier.

The mean absorbed radiation doses based on multiple time point PET imaging of three volunteers were similar to those based on mouse biodistribution data. The major organs that received relatively high doses were kidneys, liver, spleen, and heart wall. The bladder wall also received high exposure due to renal excretion of the radioactivity (0.0683±0.0090 mSv/MBq). The whole body absorbed dose was 0.0151±0.0001 mSv/MBq with an effective dose of 0.0179±0.0003 mSv/MBq.

TABLE 3

| Time (min) | Blood | Lung | Liver | Spleen | Kidneys | Stomach | S. Intestine | Pancreas | Bone | Muscle |
| --- | --- | --- | --- | --- | --- | --- | --- | --- | --- | --- |
| 5 | 7.97 ± 0.15 | 1.53 ± 0.15 | 3.80 ± 0.44 | 4.10 ± 0.36 | 4.40 ± 0.26 | 1.23 ± 0.15 | 1.73 ± 0.25 | 2.13 ± 0.40 | 2.10 ± 0.26 | 0.53 ± 0.21 |
| 10 | 7.53 ± 0.25 | 1.47 ± 0.29 | 3.70 ± 0.61 | 4.07 ± 0.47 | 4.23 ± 0.49 | 1.50 ± 0.20 | 1.57 ± 0.12 | 2.03 ± 0.15 | 1.93 ± 0.12 | 0.60 ± 0.10 |
| 15 | 7.17 ± 0.35 | 1.4 ± 0.17 | 3.73 ± 0.59 | 4.00 ± 0.52 | 4.03 ± 0.50 | 1.23 ± 0.12 | 1.73 ± 0.12 | 1.90 ± 0.26 | 1.83 ± 0.15 | 0.60 ± 0.17 |
| 30 | 6.93 ± 0.21 | 1.30 ± 0.17 | 3.57 ± 0.46 | 3.90 ± 0.61 | 3.77 ± 0.29 | 1.23 ± 0.06 | 1.63 ± 0.15 | 1.67 ± 0.15 | 1.67 ± 0.15 | 0.57 ± 0.12 |
| 45 | 6.70 ± 0.26 | 1.30 ± 0.20 | 3.50 ± 0.52 | 3.77 ± 0.57 | 3.87 ± 0.32 | 1.23 ± 0.06 | 1.63 ± 0.06 | 1.67 ± 0.15 | 1.50 ± 0.20 | 0.53 ± 0.06 |
| 60 | 6.20 ± 0.17 | 1.23 ± 0.06 | 3.47 ± 0.47 | 3.73 ± 0.42 | 3.60 ± 0.10 | 1.10 ± 0.00 | 1.47 ± 0.15 | 1.43 ± 0.15 | 1.37 ± 0.06 | 0.50 ± 0.00 |
| 75 | 6.03 ± 0.12 | 1.10 ± 0.17 | 3.43 ± 0.49 | 4.93 ± 2.10 | 3.43 ± 0.15 | 1.07 ± 0.12 | 1.33 ± 0.21 | 1.37 ± 0.21 | 1.27 ± 0.12 | 0.47 ± 0.06 |
| 90 | 5.97 ± 0.15 | 1.07 ± 0.12 | 3.33 ± 0.58 | 3.57 ± 0.55 | 3.30 ± 0.20 | 1.03 ± 0.15 | 1.17 ± 0.32 | 1.37 ± 0.31 | 1.23 ± 0.15 | 0.77 ± 0.64 |

Example 17

This example demonstrates the differential diagnosis of focal hepatic lesions, in accordance with an embodiment of the invention.

The widespread use of imaging studies has led to an increase in detection of incidental focal hepatic lesions (FLLs). Differential diagnosis of malignant and benign solid and cystic liver lesions is very important for patient management. Among the 11 patients with focal hepatic lesion(s) diagnosed by enhanced CT and/or MRI, 4 were with hemangioma. All hemangiomas showed much higher $^{68}$Ga-NEB signal intensity than the surrounding normal hepatic tissues, while no apparent difference between lesions and hepatic tissues was identified on FDG PET. The lesions were not discernable on regular CT but showed signal enhancement with CT contrast agent (FIG. 29A-29H). Hepatocellular carcinoma (HCC) showed high tracer uptake on FDG PET but with big variance from patient to patient. $^{68}$Ga-NEB showed consistently lower HCC uptake than normal hepatic tissue (FIG. 30 and FIGS. 31A-31C). Similarly, hepatic cysts and neuroendocrine liver metastases also showed low lesion/background ratio with $^{68}$Ga-NEB PET (FIG. 30).

Due to the abundant blood supply, normal liver tissue showed prominent $^{68}$Ga-NEB accumulation with a standard uptake value (SUV) of 3.73±0.47 (Table 4). The SUV of $^{68}$Ga-NEB in hemangiomas (6.83±1.38) was much higher than that in the surrounding hepatic tissue (P<0.01). All other focal hepatic lesions including HCC, hepatic cysts and neuroendocrine tumor liver metastases showed negative contrast to hepatic tissues with SUVs of 2.12±0.16, 2.13, and 2.69±0.44, respectively.

TABLE 4

|  | $^{18}$Ga-NEB | $^{18}$F-FDG |
| --- | --- | --- |
| HCC (n = 7) | 2.12 ± 0.16 | 5.96 ± 2.90 |
| NET Met (n = 4) | 2.69 ± 0.44 | 2.85 ± 0.70 |
| Hemangioma (n = 5) | 6.83 ± 1.38 | 1.19 ± 0.19 |
| Cyst (n = 1) | 2.13 | 1.21 |
| Normal hepatic tissue (n = 11) | 3.69 ± 0.53 | 1.80 ± 0.41 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of imaging a lymph node in a mammal, consisting of administering to the mammal a compound of formula (I):

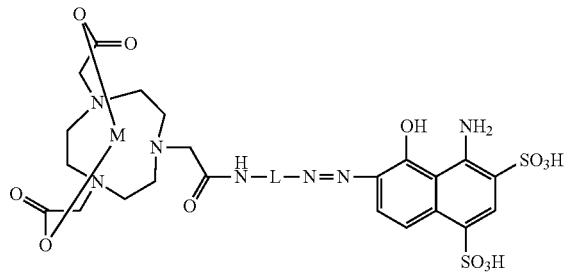

Wherein M is selected from $^{18}$F-AlF, $^{60}$Cu, $^{61}$Cu, $^{62}$Cu, $^{64}$Cu, $^{67}$Cu, $^{68}$Ga, $^{86}$Y, $^{89}$Zr, $^{111}$In, $^{99m}$Tc, $^{186}$Re, $^{188}$Re, Gd$^{3+}$, and Mn$^{2+}$, and PET imaging the mammal, and optionally, coadministering to the mammal Evans blue dye, and visually imaging the mammal.

2. The method of claim 1, wherein the compound of formula (I) is:

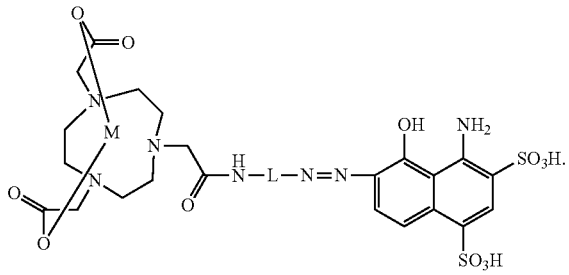

3. The method of claim 1, wherein M is $^{18}$F-AlF, $^{64}$Cu, or $^{68}$Ga.

4. The method of claim 3, wherein the compound of formula (I) is:
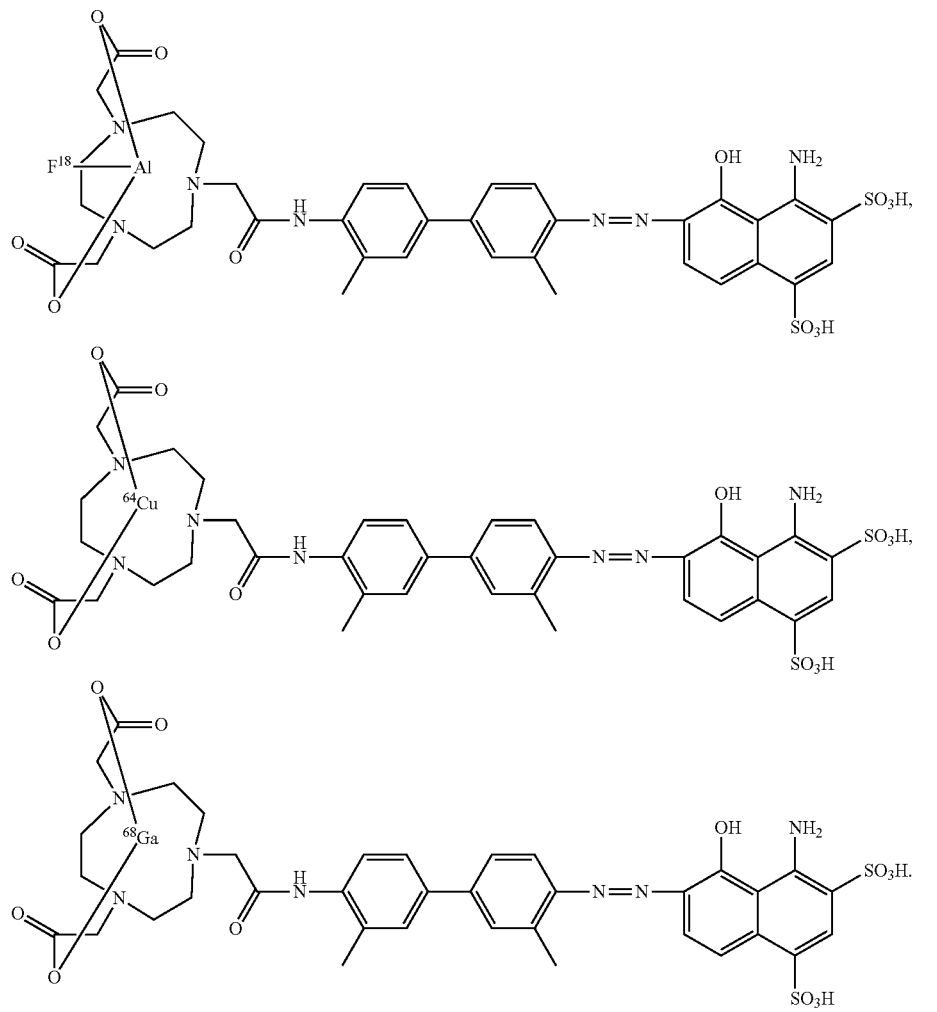
5. The method of claim 1, wherein the lymph node is a sentinel lymph node.
* * * * *